(12) United States Patent
Jinno et al.

(10) Patent No.: US 7,942,895 B2
(45) Date of Patent: May 17, 2011

(54) WORKING MECHANICAL DEVICE AND MANIPULATOR

(75) Inventors: Makoto Jinno, Ota-ku (JP); Takamitsu Sunaoshi, Yokohama (JP); Shigeru Omori, Ashigarakami-gun (JP)

(73) Assignees: Terumo Kabushiki Kaisha, Tokyo (JP); Kabushiki Kaisha Toshiba, Tokyo (JP)

( * ) Notice: Subject to any disclaimer, the term of this patent is extended or adjusted under 35 U.S.C. 154(b) by 728 days.

(21) Appl. No.: 11/833,023

(22) Filed: Aug. 2, 2007

(65) Prior Publication Data
US 2008/0039256 A1 Feb. 14, 2008

(30) Foreign Application Priority Data
Aug. 8, 2006 (JP) .................. 2006-215912

(51) Int. Cl.
*A61B 17/00* (2006.01)
(52) U.S. Cl. ....................................................... 606/205
(58) Field of Classification Search .................. 606/205, 606/206–209, 1; 600/104, 141, 142; D24/143; D8/52, 54; 433/4; 81/176.3; 294/106
See application file for complete search history.

(56) References Cited

U.S. PATENT DOCUMENTS
6,217,094 B1 4/2001 Hanaduka et al.
2002/0040217 A1 4/2002 Jinno FOREIGN PATENT DOCUMENTS
| EP | 0 606 531 A2 | 7/1994 |
|---|---|---|
| EP | 1 707 153 A1 | 10/2006 |
| JP | 55-134183 | 9/1980 |
| JP | 57-178691 | 11/1982 |
| JP | 63-102886 | 5/1988 |
| JP | 3631450 | 12/2004 |

*Primary Examiner* — Eduardo C Robert
*Assistant Examiner* — Christopher Schubert
(74) *Attorney, Agent, or Firm* — Oblon, Spivak, McClelland, Maier & Neustadt, L.L.P.

(57) ABSTRACT

A working unit comprises a gear body rotatable in a direction perpendicular to a reference axis, a gear ring including a proximal end surface held in contact with the gear body and rotatable about the reference axis to change the direction of rotation of the gear body, a first end effector body held in contact with an axially distal end surface of the gear ring at an upper portion thereof, and rotatable about a rotational axis perpendicular to the reference axis to change the direction of rotation of the gear ring, and a second end effector body held in contact with the axially distal end surface of the gear ring at a lower portion thereof, and rotatable in a direction opposite to the direction in which the first end effector body rotates, about the rotational axis. The first end effector body and the second end effector body are openable and closable symmetrically with respect to the reference axis.

8 Claims, 21 Drawing Sheets

WORKING MECHANICAL DEVICE AND MANIPULATOR

BACKGROUND OF THE INVENTION

1. Field of the Invention

The present invention relates to a working mechanical device for opening and closing a pair of end effector bodies with a power transmitting mechanism for performing certain treatments on a living body tissue, and a manipulator having such a working mechanical device on its distal end for performing manipulating actions from the other end thereof through an arm or the like.

2. Description of the Related Art

According to laparoscopic surgery, it is customary to form a plurality of holes in the abdominal part of the patient, insert an endoscope and a manipulator (or forceps) into the respective holes, and perform the surgical operation while images captured by the endoscope are being observed on a display monitor by the surgeon. Since such a laparoscopic surgical operation does not require the abdominal cavity to be opened, the burden on the patient is small and the number of days which the patient needs to recover and spend in the hospital until they are allowed to come out of hospital is greatly reduced. For these reasons, the laparoscopic surgical operation is expected to find an increased range of applications.

Manipulators for use in laparoscopic surgery are desirably capable of quick and appropriate surgical techniques depending on the position and size of the affected region, and are used to perform various surgical techniques like suture, ligature, knot-tying and removing of the affected part of the patient. The present applicant has developed and proposed a manipulator which has a high degree of freedom for manipulation and which can easily be operated (see, for example, Japanese patent No. 3631450).

The manipulator disclosed in Japanese Patent No. 3631450 includes a working unit having a pair of end effector bodies on its distal end which can be opened and closed symmetrically with respect to a reference axis. The working unit has a wide operating range, can operate in the same fashion as general tools such as pliers or the like, and can easily be manipulated.

With the working unit of the manipulator disclosed in Japanese Patent No. 3631450, the pair of end effector bodies is actuated by respective independent mechanisms to open and close grippers about an opening/closing axis and rotate the grippers about an attitude axis. Specifically, when the grippers are turned in mutually opposite directions, the grippers are opened and closed, and when the grippers are turned in the same direction, the grippers are rotated. However, the grippers are opened and closed and are rotated in the same plane. For example, when the grippers are opened and closed in horizontal directions, they are rotated also in horizontal directions, and when the grippers are opened and closed in vertical directions, they are rotated also in vertical directions. Consequently, the opening/closing axis and the attitude axis of the grippers are limited in their relative layout.

In laparoscopic surgical operations, the surgeon may find it desirable to rotate the grippers in horizontal directions and at the same time to open and close the grippers in vertical directions or vise versa for better operability depending on the living tissue to be treated or how the living tissue is to be treated. It may also be preferable to open and close the grippers in any directions with respect to the attitude axis.

SUMMARY OF THE INVENTION

It is an object of the present invention to provide a working mechanical device for actuating a pair of end effector bodies at the distal end of a working unit with a single drive mechanism and opening and closing the end effector bodies in any desired directions, and a manipulator incorporating such a working mechanical device.

A working mechanical device according to the present invention comprises a first drive rotor rotatable in a direction perpendicular to a reference axis, a first intermediary rotor including an axial proximal end surface held in contact with the first drive rotor, and rotatable about the reference axis to change the direction of rotation of the first drive rotor, a first end effector drive member held in contact with an axially distal end surface of the first intermediary rotor at one side of the center thereof, and rotatable about an opening and closing axis perpendicular to the reference axis to change the direction of rotation of the first intermediary rotor, and a second end effector drive member held in contact with an axially distal end surface of the first intermediary rotor at an opposite side of the center thereof, and rotatable in a direction opposite to the direction in which the first end effector drive member rotates, about the opening and closing axis perpendicular to the reference axis to change the direction of rotation of the first intermediary rotor.

A manipulator according to the present invention comprises the above-mentioned working mechanical device, an operation unit held by hand, an input member mounted on the operation unit and operable by hand, a rotational source rotatable based on operation of the input member, and a flexible power transmitting member.

With the working mechanical device and the manipulator according to the present invention, a pair of end effector bodies of a working unit on the distal end thereof is actuated by a single drive mechanism. The direction in which the end effector bodies are openable and closable can be set to any desired directions.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
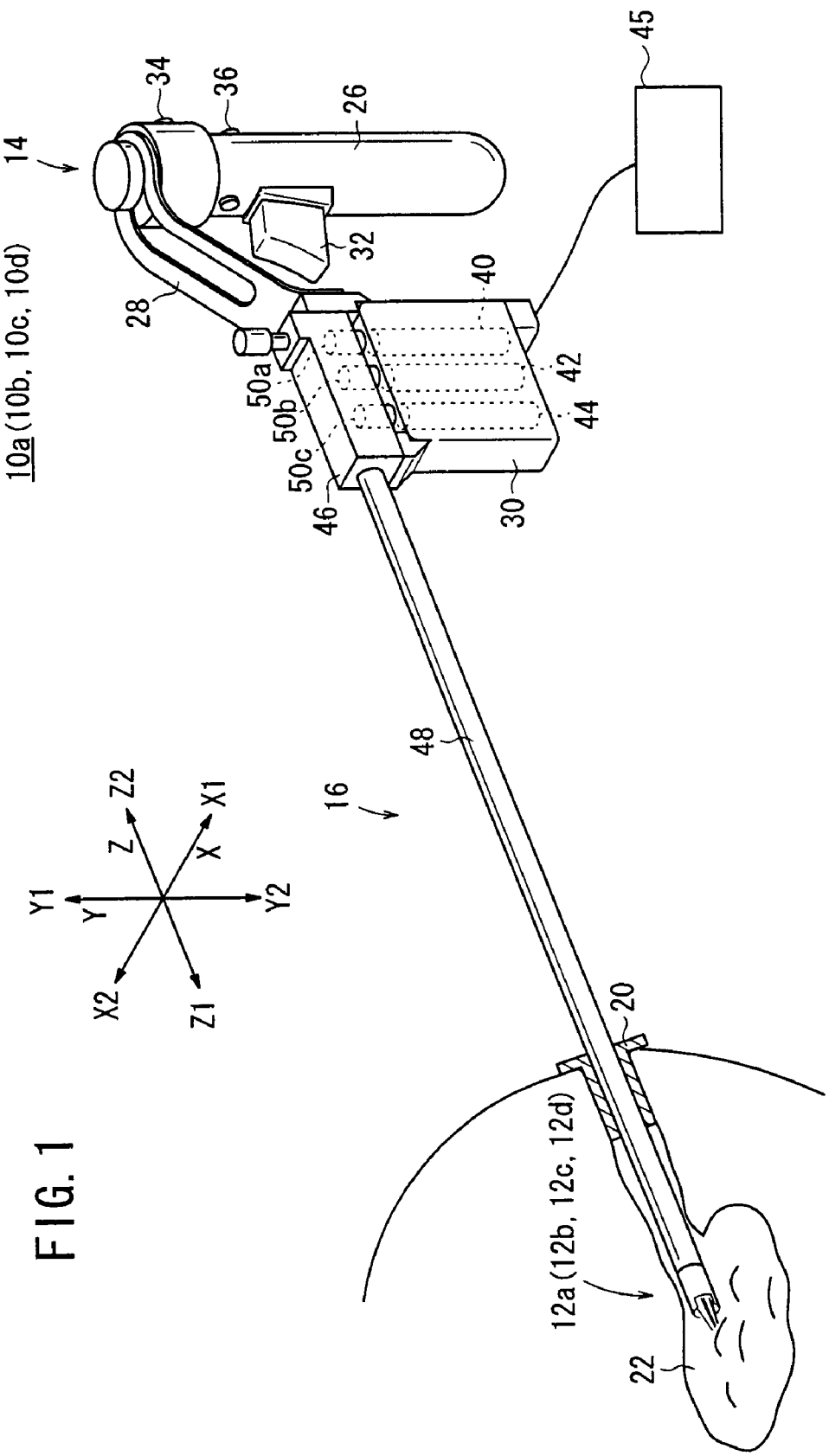
FIG. 1 is a perspective view of a manipulator according to a first embodiment of the present invention.

Working mechanical devices and manipulators according to first, second, third, and fourth embodiments of the present invention will be described below with reference to FIGS. 1 through 20. A manipulator 10a (see FIG. 1) according to a first embodiment, a manipulator 10b (see FIG. 14) according to a second embodiment, a manipulator 10c (see FIG. 16) according to a third embodiment, and a manipulator 10d (see FIG. 20) according to a fourth embodiment are typically in the form of medical manipulators for use in laparoscopic surgical operations or the like. Working units (working mechanical devices) 12a, 12b, 12c, 12d according to the first, second, third, and fourth embodiments comprise mechanisms having three degrees of freedom and mounted on the distal ends of the manipulators 10a, 10b, 10c, 10d. The working units 12a, 12b, 12c, 12d serve to grip a portion of a living tissue, a curved needle, or the like for performing a certain operation, and is usually referred to as gripping forceps or a needle driver (needle holder).

As shown in FIG. 1, the manipulator 10a comprises an operation command unit 14 on a proximal end thereof which is held and operated by hand, the working unit 12a on the distal end thereof for working on a living tissue, and an elongate connector 16 interconnecting the working unit 12a and the operation command unit 14. The working unit 12a and the connector 16 are of a small diameter and can be inserted into a body cavity 22 through a trocar 20 in the form of a hollow cylinder mounted in an abdominal region or the like of the patient. The working unit 12a is actuated by the operation command unit 14 to perform various techniques to remove, grip, suture, or tie an affected part of the patient's body in the body cavity 22.

It is assumed in the description which follows that transverse directions of each of the manipulators 10a, 10b, 10c, 10d are referred to as X directions, vertical directions as Y directions, and longitudinal directions of the connector 16 as Z directions in FIGS. 1, 14, 16, and 20. Of the X directions, the rightward direction is referred to as an X1 direction, and the leftward direction as an X2 direction. Of the Y directions, the upward direction is referred to as an Y1 direction, and the downward direction as an Y2 direction. Of the Z directions, the forward direction is referred to as a Z1 direction, and the rearward direction as a Z2 direction. Unless otherwise noted, these directions represent directions of the manipulators 10a, 10b, 10c, 10d when they are of a neutral posture (shown in FIGS. 2, 14, 16, and 20). The definition of the above directions is for illustrative purpose only, and the manipulators 10a, 10b, 10c, 10d can be used in any orientations, e.g., it may be used upside down.

The operation command unit 14 includes a grip handle 26 gripped by hand, an arm 28 extending from an upper portion of the grip handle 26, and an actuator block 30 connected to a distal end of the arm 28. The grip handle 26 includes a trigger lever (input member) 32, a first instruction lever 34, and a second instruction lever 36 which are operable by a finger. The trigger lever 32 is disposed in a position where it can easily be pulled by an index finger.

The actuator block 30 houses therein a motor (rotational source) 40, a motor 42, and a motor 44 corresponding to respective mechanisms of three degrees of freedom which are incorporated in the working unit 12a. The motors 40, 42, 44 are arrayed parallel to each other in the longitudinal direction of the connector 16. The motors 40, 42, 44 are small in size and diameter, making the actuator block 30 compact and flat in shape. The actuator block 30 is disposed downwardly of the end of the operation command unit 14 in the Z1 direction. The motors 40, 42, 44 rotate under the control of a controller 45 based on the operation of the operation command unit 14.

The connector 16 includes a joint 46 joined to the actuator block 30 and a hollow connector shaft 48 extending in the Z1 direction from the joint 46. The joint 46 houses therein a drive pulley 50a, a drive pulley 50b, and a drive pulley 50c which are rotatable and are connected respectively to the drive shafts of the motors 40, 42, 44. Wires (flexible power transmitting member) 52, 54, 56 are wound respectively around the drive pulleys 50a, 50b, 50c and extend through a space 48a (see FIG. 2) in the connector shaft 48 to the working unit 12a. The wires 52, 54, 56 may be of the same type and same diameter. The wires 52, 54, 56 will collectively be referred to as a wire 57.

The joint 46 can be operated according to a predetermined process to disconnect the connector 16 from the operation command unit 14 for cleaning, sterilization, maintenance, etc. The connector 16 and the working unit 12a can be replaced with other connectors and working units. For example, depending on the technique required for a certain surgical operation, the connector 16 may be replaced with a connector having a different length and/or the working unit 12a may be replaced with a working unit incorporating different mechanisms.

Figure 2:
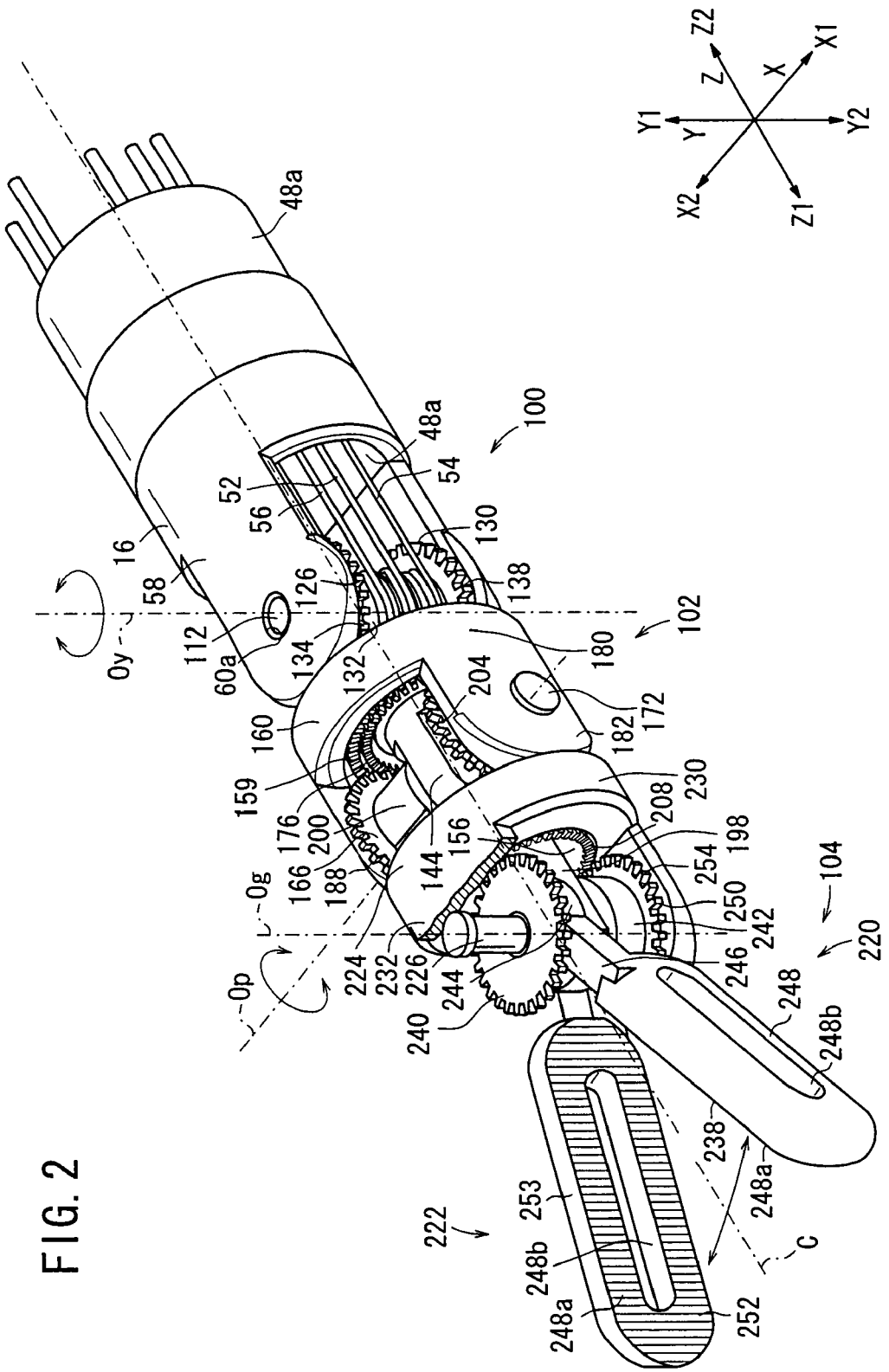
FIG. 2 is a perspective view, partly broken away, of a working unit (working mechanical device) according to the first embodiment.
Figure 3:
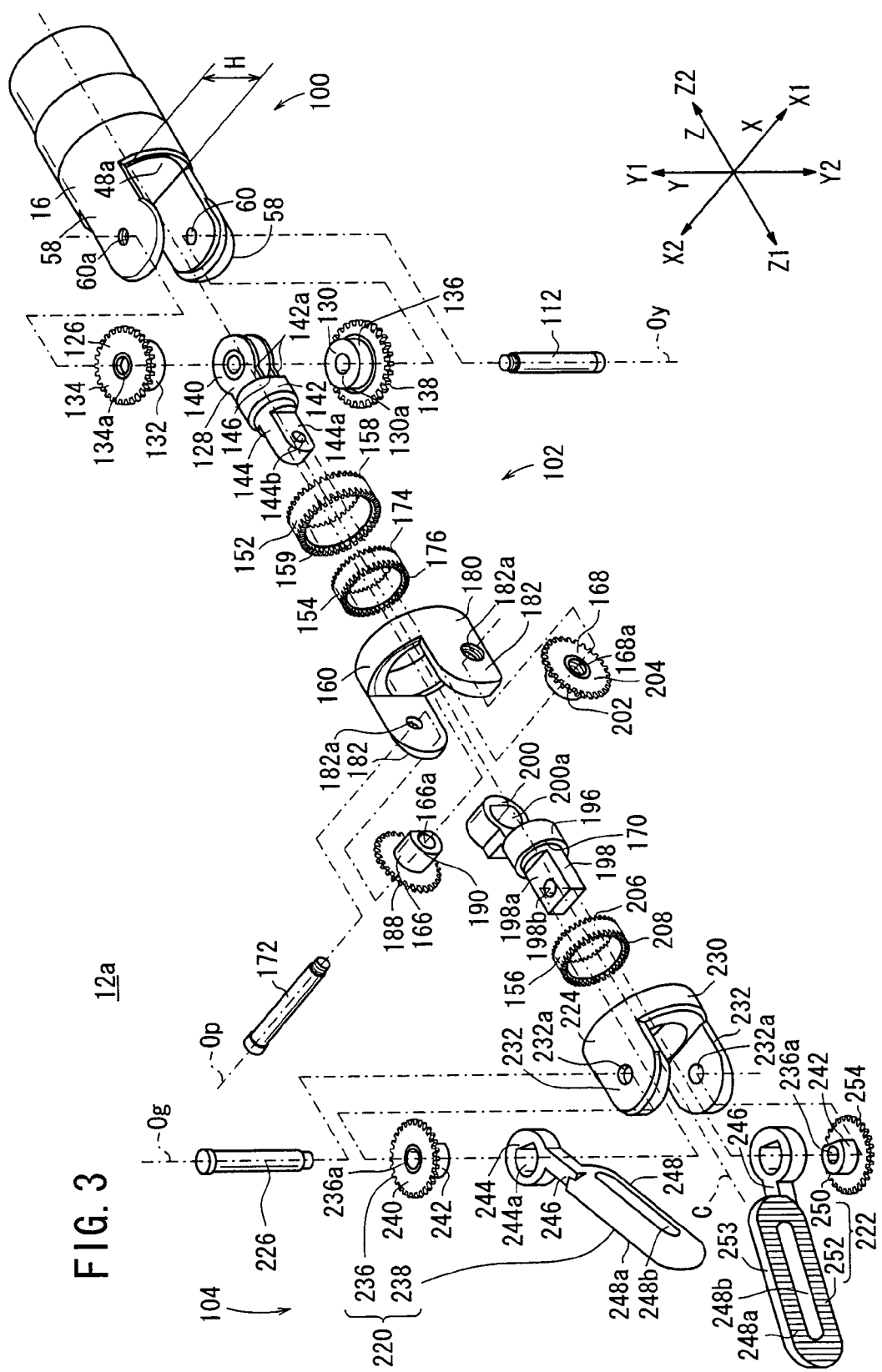
FIG. 3 is an exploded perspective view of the working unit according to the first embodiment.
Figure 4:
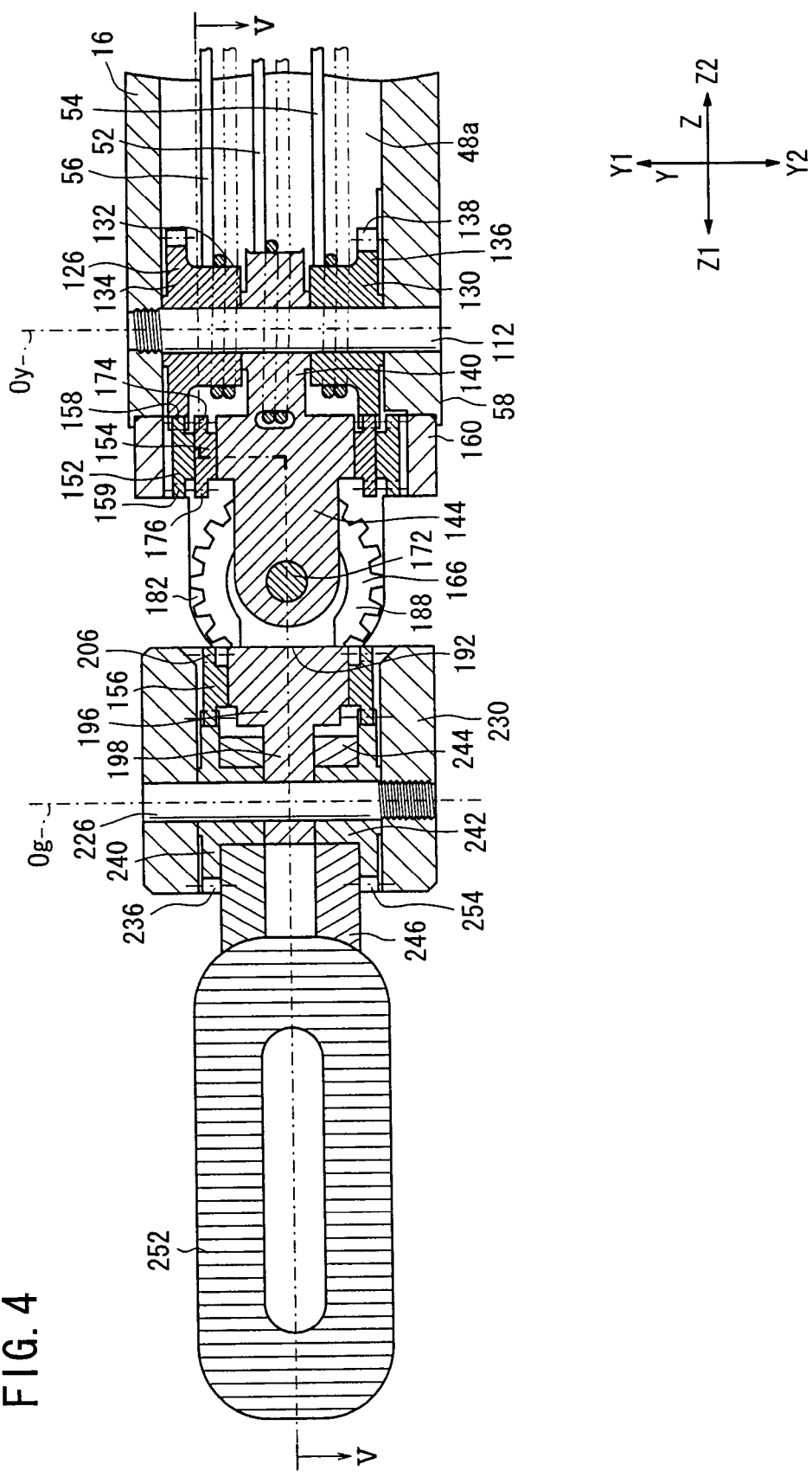
FIG. 4 is a sectional side elevational view of the working unit according to the first embodiment.
Figure 5:
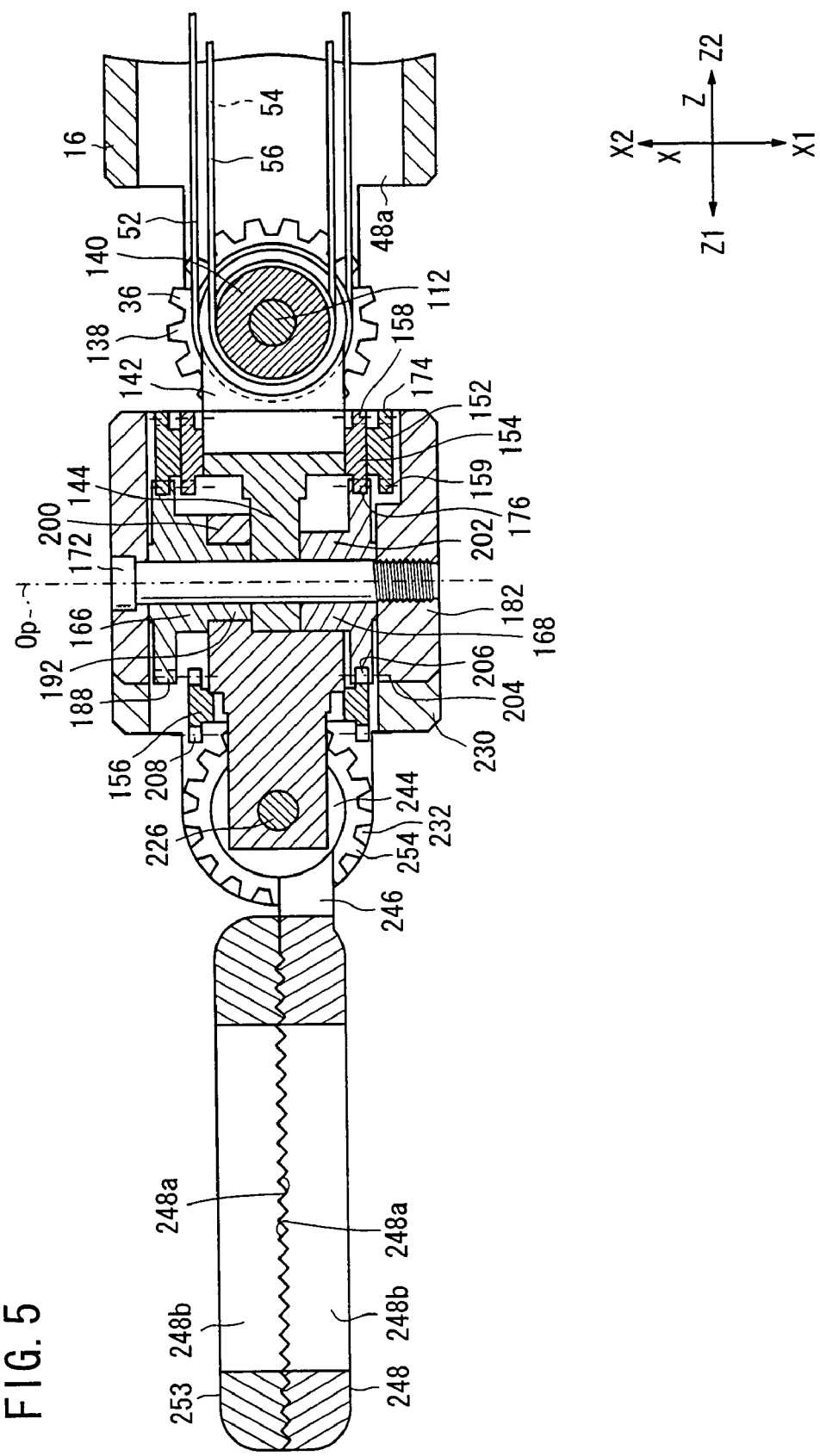
FIG. 5 is a sectional plan view of the working unit according to the first embodiment.

As shown in FIG. 2, the connector 16 has a pair of diametrically opposite tongues 58 projecting toward the distal end thereof and disposed in facing relation to the central axis of the connector shaft 48. The space 48a in the connector shaft 48 communicates with a space between the tongues 58. The tongues 58 have a pair of shaft holes 60a defined respectively therein which are held in alignment with each other. The tongues 58 have respective distal ends which are in arc shapes. The pair of tongues 58 has respective flat inner surfaces facing each other which extend parallel to each other and which are spaced from each other by a distance H. The two shaft holes 60a are disposed one on each side of the central axis of the connector 16.

As shown in FIG. 2, the working unit 12a incorporates therein mechanisms of three degrees of freedom. These mechanisms include a mechanism having a first degree of freedom for angularly moving a portion of the working unit 12a that is positioned ahead of a first rotational axis Oy extending along the Y directions, in yawing directions about the first rotational axis (pivot) Oy, a mechanism having a second degree of freedom for angularly moving the portion of the working unit 12a in pitching directions about a second rotational axis (pivot) Op extending along the X directions, and a mechanism having a third degree of freedom for opening and closing an end effector 104 on the distal end of the working unit 12a about a third rotational axis Og. The working unit 12a comprises a wire-driven mechanism 100, a drive mechanism 102, and the end effector 104. Though the drive mechanism 102 and the end effector 104 will hereinafter be described separately from each other for convenience, since the term "end effector" is generally interpreted as a mechanism on an arm end for performing a certain action, the end effector 104 and the drive mechanism 102 may be defined as an integrated end effector.

The wire-driven mechanism 100, the drive mechanism 102, and the end effector 104 will be described in detail below with reference to FIGS. 2 through 5.

The wire-driven mechanism 100 is disposed between the tongues 58 and serves to convert circulative movements of the respective wires 52, 54, 56 into rotational movements and transmit the rotational movements to the drive mechanism 102. The wire-driven mechanism 100 includes a shaft 112 inserted in the shaft holes 60a. The shaft 112 is threaded, press-fitted or welded securely in the shaft holes 60a. The shaft 112 is axially aligned with the first rotational axis Oy.

The wire-driven mechanism 100 comprises a gear body (second drive rotor) 126, a main shaft 128, and a gear body (driven tubular member) 130 which are rotatably supported on the shaft 112 and arranged successively in the order named in the Y2 direction.

The gear body 126 comprises a tubular member 132 and a first gear 134 disposed concentrically on an upper portion of the tubular member 132. The first gear 134 has a low annular rib 134a disposed on the upper surface thereof around the hole through which the shaft 112 is inserted. The annular rib 134a prevents the upper surface of the first gear 134 from contacting the upper tongue 58, thereby reducing the sliding resistance that is imposed on the first gear 134 by the upper tongue 58.

Figure 6:
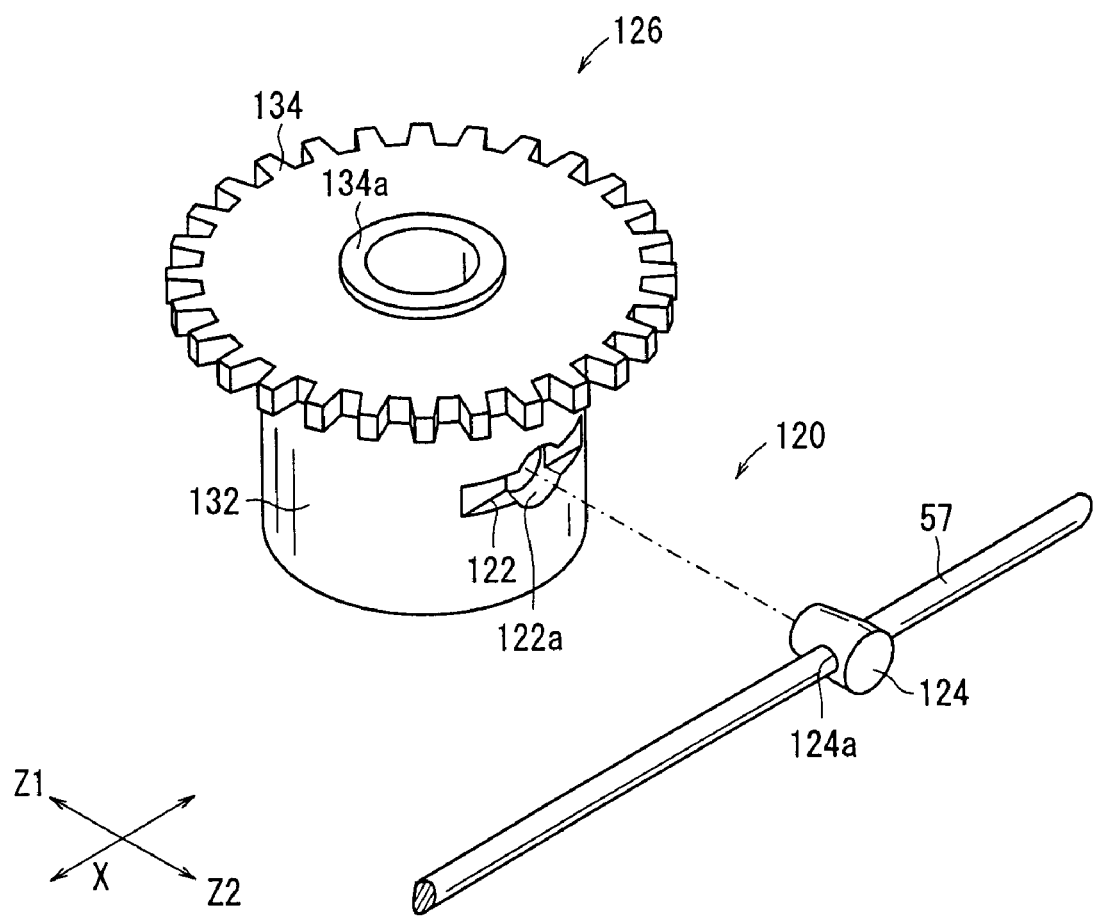
FIG. 6 is an exploded perspective view of a wire securing mechanism.

As shown in FIG. 6, the tubular member 132 is combined with a wire securing mechanism 120. The wire securing mechanism 120 has a groove 122 defined in an upper portion of the side of the tubular member 132 which faces the Z2 direction and extending laterally in the X directions when the gear body 126 is in a neutral position, and a tapered fastening pin 124 disposed centrally in the groove 122. The groove 122 has a recess 122a positioned at the center of the fastening pin 124 to be inserted and fixed therein. The groove 122 may be slightly inclined in alignment with a turn of the wire 57 that is helically wound around the tubular member 116.

The groove 122 has a width and a maximum depth that are essentially equal to the diameter of the wire 57. The fastening pin 124 has a hole 124a defined laterally therethrough for the wire 57 to extend therethrough. The wire 57 is threaded through the hole 124a and the fastening pin 124 is inserted into the recess 122a, holding the wire 57 partly in the groove 122. The wire 57 is thus oriented horizontally and fastened to the tubular member 132.

As shown in FIGS. 2 through 5, the gear body 130 is essentially identical in shape to the gear body 126, but is in an upside-down orientation with respect to the gear body 126. The gear body 130 comprises a tubular member 136 and a second gear 138 disposed concentrically on a lower portion of the tubular member 136. The tubular member 136 is substantially identical in diameter and shape to the tubular member 132. The tubular member 136 is combined with a wire securing mechanism 120, which is similar to the wire securing mechanism 120 of the tubular member 116, on the side of the tubular member 136 which faces the Z2 direction, and the wire 54 is fastened to the tubular member 136 by the wire securing mechanism 120.

The main shaft 128 has a tubular member (second tubular member) 140 through which the shaft 112 extends, a cylindrical member 142 coupled to the tubular member 140 and facing the Z1 direction, and a pitch base 144 extending from the center of the cylindrical member 142 in the Z1 direction. The pitch base 144 is a member serving as a basis for movement in the pitching directions, and includes a pair of laterally spaced parallel slide surfaces 144a for defining movement in the pitching directions and a hole 144b defined in a distal end thereof and extending between the slide surfaces 144a. The hole 144b serves as the center of rotation of the end effector 104.

The cylindrical member 142 is slightly spaced from an outer side surface of the tubular member 140 with two upper and lower bridges 142a interposed therebetween. A vertical hole 146 which is slightly elongate in the Y directions is defined between the cylindrical member 142 and the tubular member 140 for receiving the wire 52 to extend therethrough. The tubular member 140 is combined with a wire securing mechanism 120, which is similar to the wire securing mechanism 120 of the tubular member 116, on the side of the tubular member 140 which faces the Z2 direction, and the wire 52 is fastened to the tubular member 140 by the wire securing mechanism 120.

In response to circulative movement of the wire 52, the main shaft 128 rotates in the yawing directions about the first rotational axis Oy to cause the pitch base 144 to swing in an XZ plane.

The tubular member 140, the gear body 126, and the gear body 130 are stacked together along the shaft 112 and have a combined height which is essentially equal to the height H such that they are disposed with substantially no clearances between the tongues 58.

The drive mechanism 102 comprises a gear ring 152, a gear ring (second intermediary rotor) 154, a gear ring (first intermediary rotor) 156, a cover 160, a gear body 166, a gear body (first drive rotor) 168, an end effector main shaft 170, and a securing pin 172.

The gear ring 154 is held in mesh with the second gear 138. Consequently, the gear ring 154 is rotatable about a reference axis C of the working unit 12a in response to rotation of the tubular member 136.

The gear ring 152 is in the form of a thin tubular member including a face gear 158 on an end face thereof facing the Z2 direction and a face gear 159 on an end face thereof facing the Z1 direction. The gear ring 152 is fitted over the gear ring 154 for sliding rotation with respect to the outer circumferential surface of the gear ring 154. The face gear 158 is in mesh with the first gear 134, so that the gear ring 152 is rotatable about the reference axis C in response to rotation of the gear body 126.

The gear ring 154 is also in the form of a thin tubular member including a face gear 174 on an end face thereof (proximal end face) facing the Z2 direction and a face gear 176 on an end face thereof (distal end face) facing the Z1 direction. The gear ring 154 is fitted over the cylindrical member 142 for sliding rotation with respect to the outer circumferential surface of the cylindrical member 142. The face gear 174 is held in mesh with the second gear 138, so that the gear ring 154 is rotatable about the reference axis C in response to rotation of the gear body 130.

The gear ring 154 allows a space to be created between the gear body 130 and the gear ring 156. Drive mechanisms for actuating the end effector 104 to operate in pitching, yawing, and rolling directions can be disposed in the space. The end effector 104 can be opened and closed while it can also be operated in the pitching, yawing, and rolling directions by those drive mechanisms.

The cover 160 serves to protect and support the components of the drive mechanism 102. The cover 160 includes a short tube 180 extending in the Z2 direction and a pair of ears 182 projecting in the Z1 direction from respective opposite side portions of the short tube 180. The ears 182 have respective holes 182a defined therein for inserting and securing the securing pin 172 therein. One of the holes 182a is a hole for inserting the securing pin 172 therethrough, and the other hole 182a is a hole for threading the securing pin 172 therein. The ears 182 have respective parallel surfaces confronting each other, and have such a width that the gear bodies 166, 168, an engaging member 200, and the pitch base 144 are slidably held by the ears 182. The short tube 180 has an inner circumferential surface whose diameter is slightly greater than the diameter of the outer circumferential surface of the gear ring 152, with a clearance left therebetween.

The cover 160 (or a cover 224 to be described later) may be in the form of a hollow cylindrical or conical cover for covering the drive mechanism 102 and the end effector 104 almost in their entirety to the extent that the operation of the drive mechanism 102 and the end effector 104 will not be hampered.

The gear body 166 is positioned in a region between the ears 182 and is displaced in the X2 direction from the center of the cover 160, and includes a third gear 188 and a boss 190 coupled centrally to the third gear 188 in concentric alignment therewith and having a D-shaped cross section. The gear body 166 is oriented such that the third gear 188 faces the X2 direction. The third gear 188 is held in mesh with the face gear 159. The gear body 166 has a central hole 166a defined therein through which the securing pin 172 is inserted.

The end effector main shaft 170 comprises a base cylindrical member 196, a gripper base 198 extending in the Z1 direction from the center of the cylindrical member 196, and an engaging member 200 projecting in the Z2 direction from a surface of the cylindrical member 196 which faces the Z2 direction at a position that is slightly displaced in the X2 direction from the center of the cylindrical member 196.

The gripper base 198 is a member providing a reference for opening and closing grippers. The gripper base 198 has a pair of upper and lower slide surfaces 198a for defining opening and closing movement of the grippers, and a hole 198b defined in a distal end portion of the gripper base 198 to provide a center of rotation of the grippers.

The engaging member 200 has a hole 200a of a D-shaped cross section in which the boss 190 engages. When the boss 190 is inserted into the hole 200a, the end effector main shaft 170 is integrally and stably combined with the gear body 166.

The gear body 168 is positioned in a region between the ears 182 which is displaced in the X1 direction from the center of the cover 160, and includes a tubular member 202 and a fourth gear 204 coupled to an end surface of the tubular member 202 in concentric alignment therewith. The gear body 168 is oriented such that the fourth gear 204 faces the X1 direction. The fourth gear 204 is held in mesh with the face gear 176. The gear body 168 has a central hole 168a defined therein through which the securing pin 172 is inserted.

The assembly of the gear body 168, the pitch base 144, the end effector main shaft 170, and the gear body 166 is disposed with substantially no clearances between the ears 182. The securing pin 172 is inserted through the holes 166a, 144b, 168a and supported therein. The assembly of the end effector main shaft 170 and the gear body 166 is swingable about the second rotational axis Op in response to rotation of the gear ring 152. The gear body 168 is rotatable in response to rotation of the gear ring 154.

The gear ring 156, which is identical in shape to the gear ring 154, includes a face gear 206 on an end face thereof (proximal end face) facing the Z2 direction and a face gear 208 on an end face thereof (distal end face) facing the Z1 direction. The gear ring 156 is fitted over the cylindrical member 196 for sliding rotation with respect to the outer circumferential surface of the cylindrical member 196. The face gear 206 is held in mesh with the fourth gear 204, so that the gear ring 156 is rotatable about the reference axis C in response to rotation of the fourth gear 204.

In the drive mechanism 102, the rotation of the gear body 126 and the first gear 134 is transmitted through the gear ring 152 and the third gear 188 to the gripper base 198, which is angularly lifted or lowered about the second rotational axis Op. The rotation of the gear body 130 and the second gear 138 is transmitted through the gear ring 154 and the fourth gear 204 to the gear ring 156 to rotate the gear ring 156 in the rolling directions.

The end effector 104 comprises a first end effector body 220, a second end effector body 222, a cover 224, and a securing pin (opening and closing shaft) 226. The securing pin 226 is aligned with the third rotational axis (opening and closing axis) Og.

The cover 224 serves to protect and support the components of the end effector 104, and is identical in shape to the cover 160. The cover 224 is angularly displaced 90° from the cover 160. The cover 224 includes a short tube 230 extending in the Z2 direction and a pair of ears 232 projecting in the Z1 direction from respective opposite upper and lower portions of the short tube 230. The ears 232 have respective holes 232a defined therein for inserting and securing the securing pin 226 therein.

The first end effector body 220 comprises a gear body 236 and a working unit 238. The gear body 236 is positioned in a region between the ears 232 which is displaced in the Y1 direction from the center of the cover 224, and includes a fifth gear 240 and a boss 242 of a D-shaped cross section which projects in the Y2 direction from the center of the fifth gear 240. The gear body 236 includes a hole 236a through which the securing pin 226 is inserted. The gear body 236 is oriented such that the fifth gear 240 faces the Y1 direction. The fifth gear 240 is held in mesh with the face gear 208 at its crest in the Y1 direction.

The working unit 238 comprises a proximal end tube 244, an arm 246 projecting substantially radially from the proximal end tube 244, and a gripper 248 projecting radially from the arm 246. The arm 246 operates as a first end effector drive member. The proximal end tube 244 has a hole 244a of a D-shaped cross section defined centrally therein for receiving the boss 242 snugly therein. Therefore, the hole 244a serves to position the boss 242 and prevent the boss 242 from rotating about its own axis.

The gripper 248 is thicker than the proximal end tube 244 and the arm 246 in the Y2 direction, and has an intermediate height region lying substantially flush with the end surfaces of the proximal end tube 244 and the arm 246 which face the Y2 direction. The gripper 248 has opposite ends which are arcuate in shape, and includes parallel ridges disposed on an inner side surface 248a and extending in the Y directions. The ridges serve to prevent a living tissue gripped by the gripper 248 from slipping. The gripper 248 has an oblong hole 248b defined therein along its longitudinal axis.

The second end effector body 222 comprises a gear body 250 and a working unit 252. The working unit 252 includes a gripper 253 which is identical in shape to the gripper 248. The arm 246 of the working unit 252 operates as a second end effector drive member. The gear body 250 is positioned in a region between the ears 232 which is displaced in the Y2 direction from the center of the cover 224, and includes a sixth gear 254. The gear body 250 is oriented such that the sixth gear 254 faces the Y2 direction. The sixth gear 254 is held in mesh with the face gear 208 at its crest in the Y2 direction. The gear body 250 is identical in shape to the gear body 236. The sixth gear 254 corresponds to the fifth gear 240. Other parts of the gear body 250 which are identical to those of the gear body 236 are denoted by identical reference characters, and will not be described in detail below.

The working unit 252 is identical in shape to the working unit 238 and is held in engagement with the gear body 250. The working unit 252 is in an upside-down orientation with respect to the working unit 238. Those parts of the working unit 252 which are identical to those of the working unit 238 denoted by identical reference characters, and will not be described in detail below.

The gripper 248 of the first end effector body 220 is displaced in the X1 direction from the gripper 253 of the second end effector body 222, and the gripper 253 of the second end effector body 222 is displaced in the X2 direction from the gripper 248 of the first end effector body 220. The grippers 248, 253 are disposed symmetrically with respect to the reference axis C such that their inner side surfaces 248a face each other.

The gear body 236, the gripper base 198, and the gear body 250 are stacked together along the securing pin 226 such that they are disposed with substantially no clearances between the ears 232. The securing pin 226 is inserted and supported in the holes 236a, 198b, and 236a.

When the gear ring 156 rotates about its own axis, the fifth gear 240 and the sixth gear 254 rotate respectively in opposite directions. Specifically, when the gear ring 156 rotates clockwise as viewed in front elevation, the fifth gear 240 rotates clockwise about the third rotational axis Og as viewed in plan, and the sixth gear 254 rotates counterclockwise about the third rotational axis Og as viewed in plan. The arms 246 and the grippers 248, 253 are rotated in the XZ plane symmetrically with respect to the reference axis C in a direction to perform the opening and closing movement.

Figure 7:
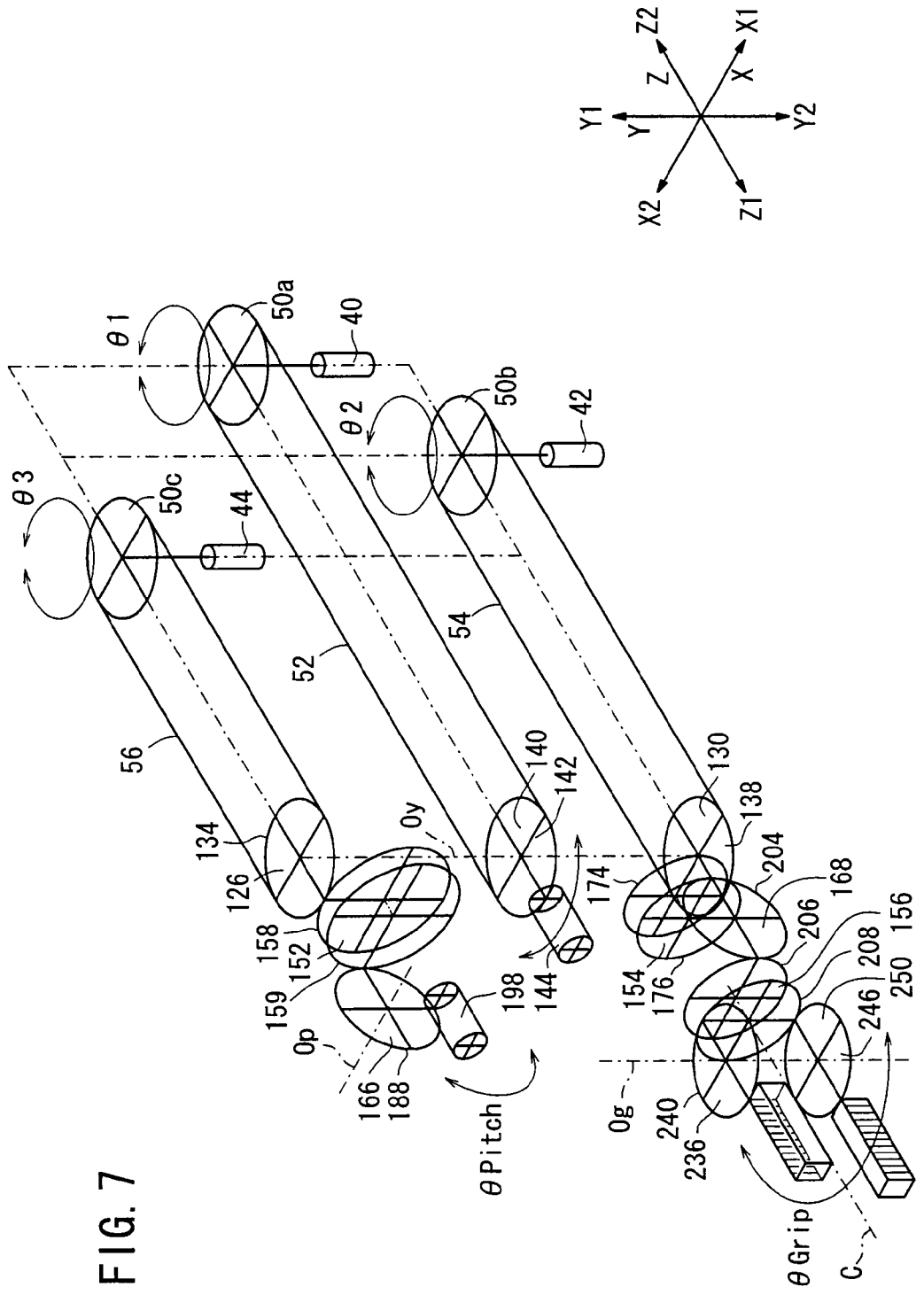
FIG. 7 is a schematic perspective view of an actuating system of the manipulator according to the first embodiment.

Operation of the manipulator 10a thus constructed will be described below with reference to FIG. 7.

First, the manipulator 10a is actuated in a yawing direction by operating the first instruction lever 34 (see FIG. 1) with a finger. Specifically, when the surgeon who handles the manipulator 10a operates the first instruction lever 34 with a finger, the motor 40 (see FIG. 1) is energized to rotate the drive pulley 50a to circulatively move the wire 52, rotating the main shaft 128 about the first rotational axis Oy. The drive mechanism 102 and the end effector 104 that are connected to the pitch base 144 of the main shaft 128 are now caused to swing in the yawing direction.

The first instruction lever 34 is tiltable selectively in normal and reverse directions. When the first instruction lever 34 is tilted in a direction, the end effector 104 is actuated in a corresponding one of the yawing directions, i.e., in a normal direction or a reverse direction. When the surgeon returns the first instruction lever 34 to its neutral position, the motor 40 is de-energized, holding the end effector 104 in the position reached in the yawing direction at the moment. Alternatively, the end effector 104 may be instructed to swing through an angle in a yawing direction which is proportional to the angle through which the first instruction lever 34 is angularly moved. The end effector 104 may be instructed to move at a certain speed or to move to a certain position (or through a certain angle).

The manipulator 10a is actuated in a pitching direction by operating the second instruction lever 36 (see FIG. 1) with a finger. Specifically, when the surgeon operates the second instruction lever 36 with a finger, the motor 42 (see FIG. 1) is energized to rotate the drive pulley 50c to circulatively move the wire 56, rotating the gear body 126, whose rotation is transmitted through the first gear 134, the face gears 158, 159 and the third gear 188 to the gear body 166. The gear body 166 is now angularly lifted or lowered in unison with the gripper base 198 about the second rotational axis Op.

The manipulator 10a is actuated in pitch selectively in normal and reverse directions depending on the direction in which the second instruction lever 36 is tilted. When the surgeon returns the second instruction lever 36 to its neutral position, the motor 44 is de-energized, holding the end effector 104 in the position reached in the pitching direction at the moment. Alternatively, the end effector 104 may be instructed to turn through an angle in a pitching direction which is proportional to the angle through which the second instruction lever 36 is angularly moved. The end effector 104 may be instructed to move at a certain speed or to move to a certain position (or through a certain angle).

The end effector 104 is selectively opened and closed by pulling the trigger lever 32 (see FIG. 1) with a finger. Specifically, when the surgeon pulls the trigger lever 32 with a finger, the motor 42 (see FIG. 1) is energized to rotate the drive pulley 50b to circulatively move the wire 54, rotating the gear body 130, whose rotation is transmitted through the second gear 138, the face gears 174, 176, the fourth gear 204, and the face gear 208 to rotate the fifth gear 240 and the first end effector body 220 in one direction and to rotate the sixth gear 254 and the second end effector body 222 in the opposite direction. The end effector 104 is thus opened or closed.

The trigger lever 32 can be pulled by a finger, and return to its original position under resiliency when it is released from the finger. The end effector 104 operates in ganged relation to the trigger lever 32 such that the end effector 104 is closed when the trigger lever 32 is pulled and returns to its open position when the trigger lever 32 is released. The trigger lever 32 may be combined with a latch mechanism for locking the trigger lever 32 in the open or closed position.

The working unit 12a allows the end effector 104 to move in yawing and pitching directions independently of the manner in which the end effector 104 operates on its own, i.e., the end effector 104 is opened and closed.

Figure 21:
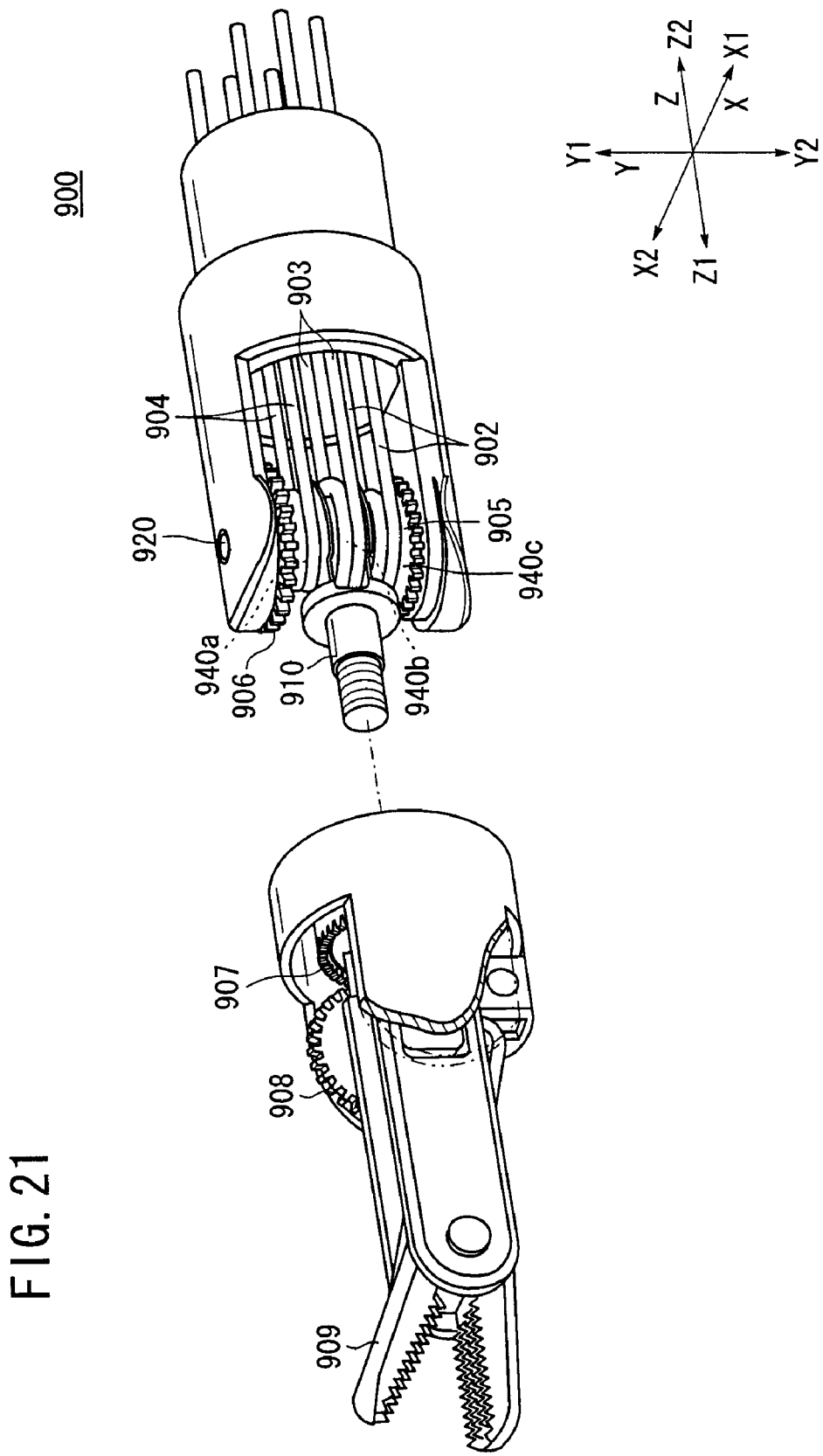
FIG. 21 is an exploded perspective view of a working unit.

The working unit 12a is of a simple structure having three degrees of freedom as with the working unit 900 shown in FIG. 21, but is smaller in size and lightweight than the working unit 900. Therefore, the working unit 12a is suitable for use in operations in narrow regions. Particularly, since the gear ring 156 that is provided to synchronize the first and second end effector bodies 220, 222 in operation is of a small-diameter tubular shape, the working unit 12a (and working units 12b through 12d) remains relatively small in diameter. Though the working unit 12a is axially long somewhat because it requires a space for installing the gear ring 156 therein, the axially long working unit 12a does not pose problems as it is a mechanism mounted on the distal end of the elongate connector shaft 48.

As the working unit 12a can be small in diameter as with the working unit 900, the trocar 20 (see FIG. 1) that is placed in an abdominal or chest part of the patient in combination with the working unit 12a can also be small in size and diameter. Accordingly, the working unit 12a is minimally invasive to the patient. The gear ring 156 allows the rotation to be transmitted simply and reliably to the fifth gear 240 and the sixth gear 254.

By controlling the motors 40, 42, 44, the opening and closing movement of the end effector 104 and the movement of the two degrees of freedom can be placed in any desired directions for orienting the end effector 104 in a combination of yawing and pitching (or rolling) directions. In other words, the axes of the working unit 12a can be placed in a pattern suitable for the operation of the manipulator 10a, thereby giving high operability to the manipulator 10a.

The end effector 104 of the working unit 12a is not limited to being opened and closed in the XZ plane, but may be opened and closed in any of various orientations depending on the object to be handled by the manipulator or the selection that the surgeon has made. Modifications of the working unit for orienting the end effector 104 in different directions will be described below with reference to FIGS. 8 through 13. Details of modifications and other embodiments to be described below which are identical to those of the manipulator 10a and the working unit 12a will be denoted by identical reference characters and will not be described in detail below.

Figure 8:
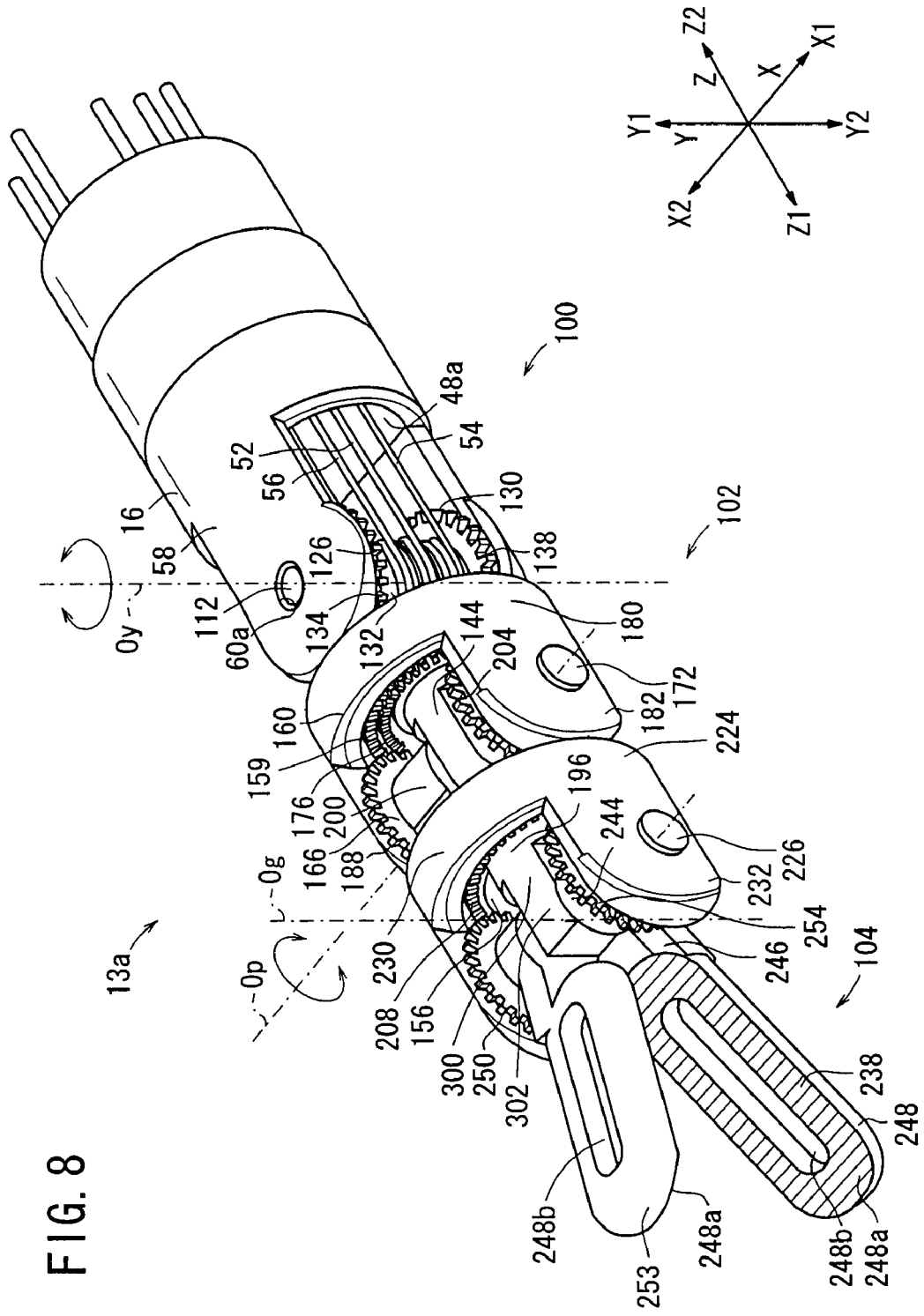
FIG. 8 is a perspective view of a first modification of the working unit according to the first embodiment.
Figure 9:
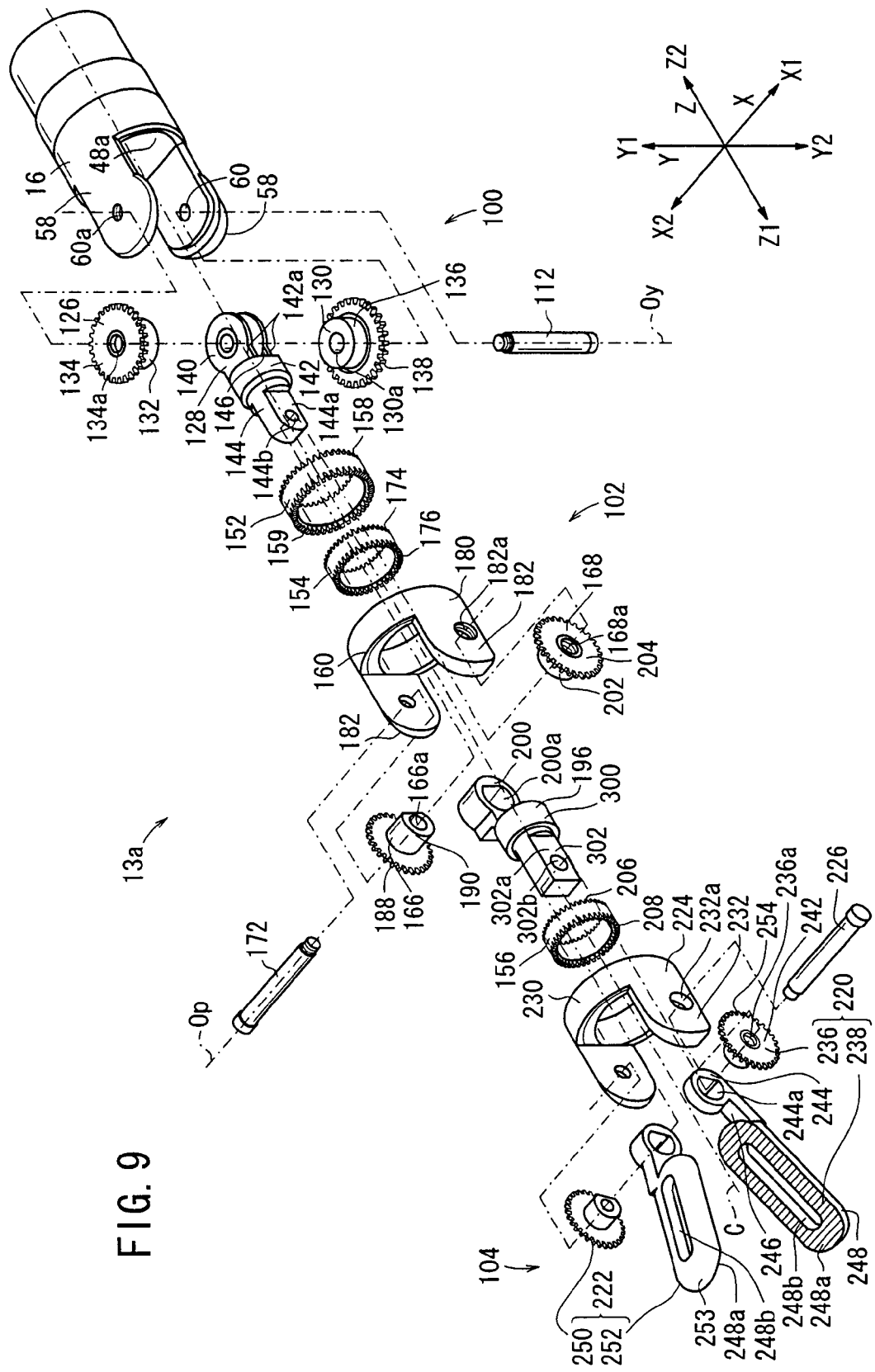
FIG. 9 is an exploded perspective view of the first modification of the working unit according to the first embodiment.

As shown in FIGS. 8 and 9, a working unit 13a according to a first modification causes the end effector 104 to be opened and closed in an YZ direction, and differs from the working unit 12a in that it includes an end effector main shaft 300 in place of the end effector main shaft 170. The end effector main shaft 300 includes a gripper base 302, which corresponds to the gripper base 198, having a pair of laterally spaced parallel slide surfaces 302a, which lie in the Y directions, for defining opening and closing movement of the grippers and a hole 302b defined in a distal end thereof and extending between the slide surfaces 302a. The hole 302b serves as the center of rotation of the end effector 104.

The gripper base 302 is angularly displaced 90° from the gripper base 198 of the working unit 12a. Therefore, the first end effector body 220 and the second end effector body 222 of the end effector 104 are opened and closed in the YZ plane.

Figure 10:
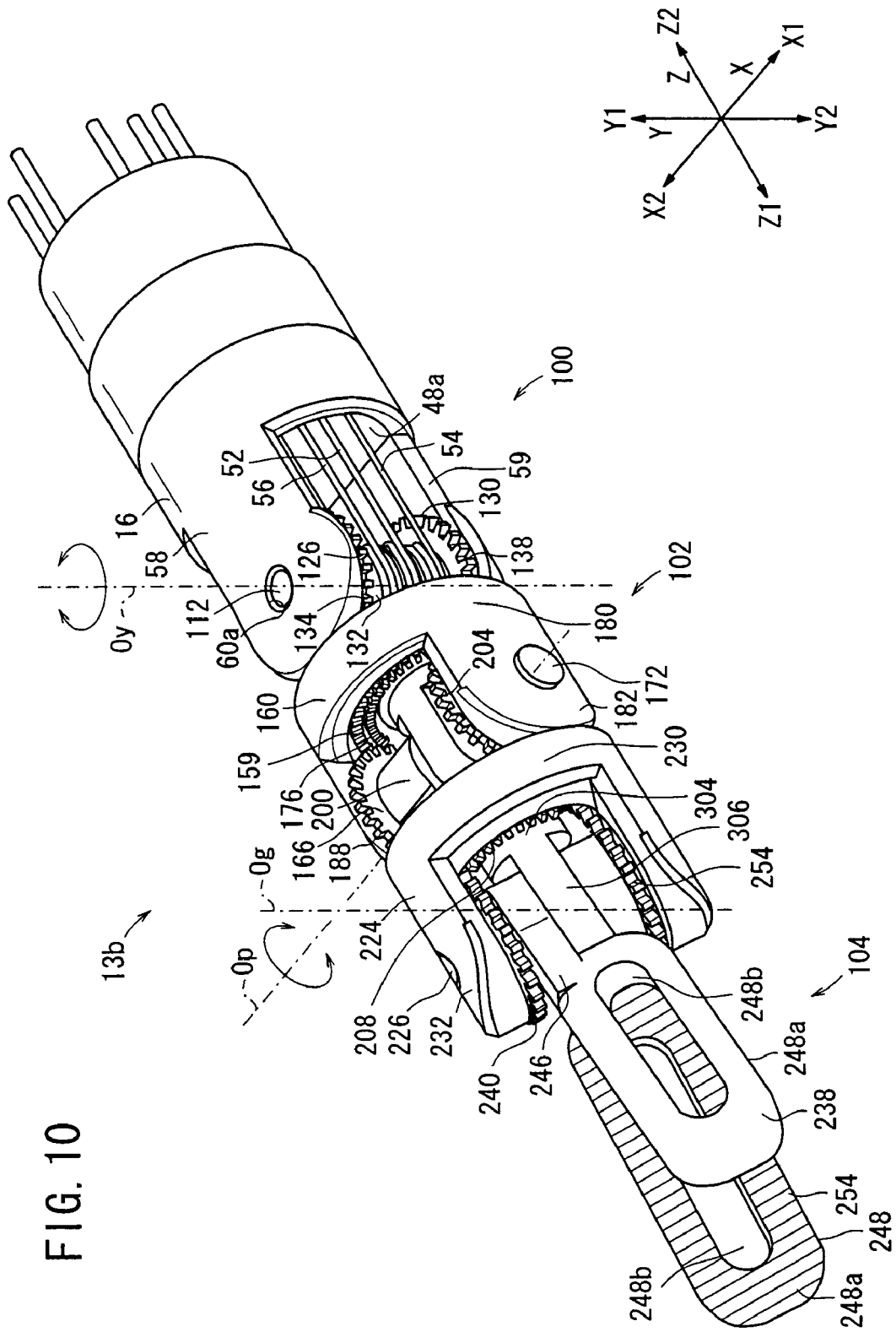
FIG. 10 is a perspective view of a second modification of the working unit according to the first embodiment.
Figure 11:
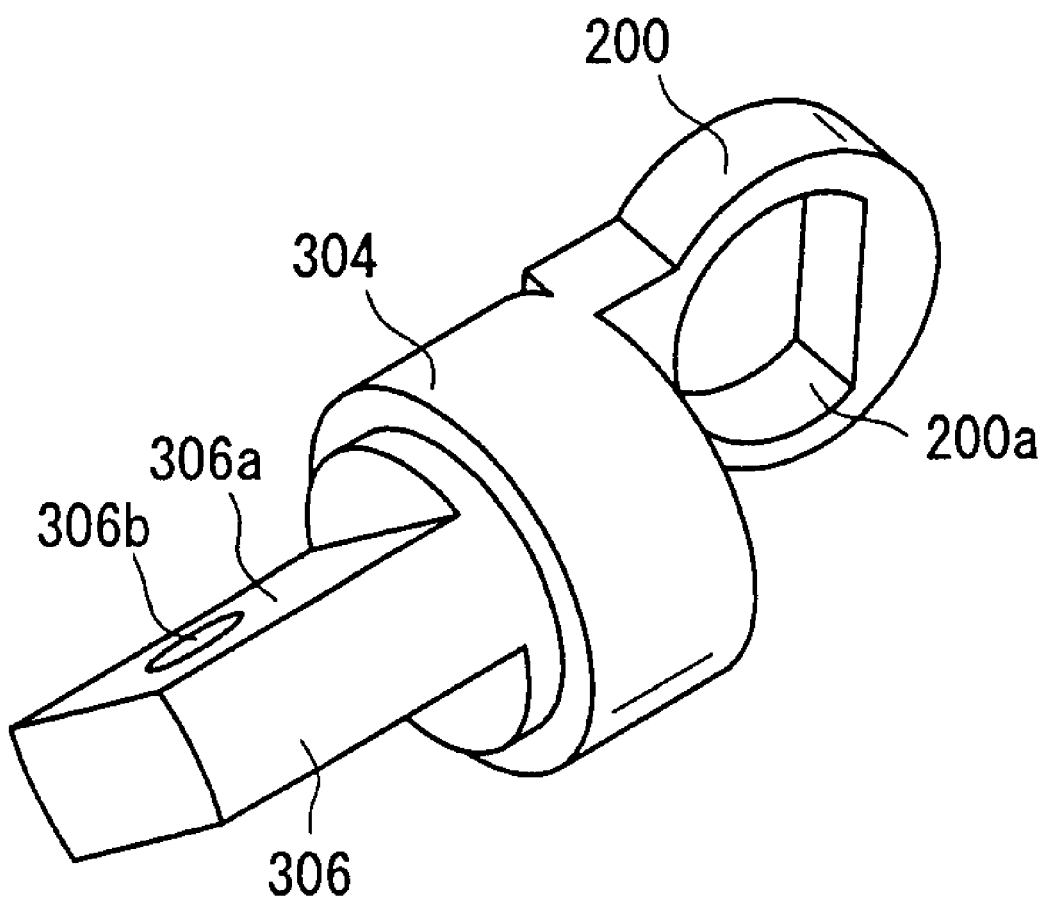
FIG. 11 is a perspective view of an end effector main shaft incorporated in the first modification shown in FIG. 10.

As shown in FIG. 10, a working unit 13b according to a second modification causes the end effector 104 to be opened and closed in a plane that is 45° inclined to the XZ plane, and differs from the working unit 12a in that it includes an end effector main shaft 304 in place of the end effector main shaft 170. As shown in FIG. 11, the end effector main shaft 304 has a gripper base 306, which corresponds to the gripper base 198, having a pair of laterally spaced parallel slide surfaces 306a, which lie in a plane that is 45° inclined to the XZ plane, for defining opening and closing movement of the grippers and a hole 306b defined in a distal end thereof and extending between the slide surfaces 306a. The hole 306b serves as the center of rotation of the end effector 104.

Since the gripper base 306 is 45° inclined to the gripper base 198, the first end effector body 220 and the second end effector body 222 of the end effector 104 are opened and closed in the plane that is 45° inclined to the XZ plane.

The angle of the securing pin 226 with respect to the shaft 112 and the securing pin 172 is not limited to 45°, but may be any angle depending on design conditions and the user's demand based on the configuration of the end effector main shaft 304. The securing pin 226 may extend parallel to, perpendicular to, or at any other angles to the shaft 112 and the securing pin 172 as viewed in plan.

Figure 12:
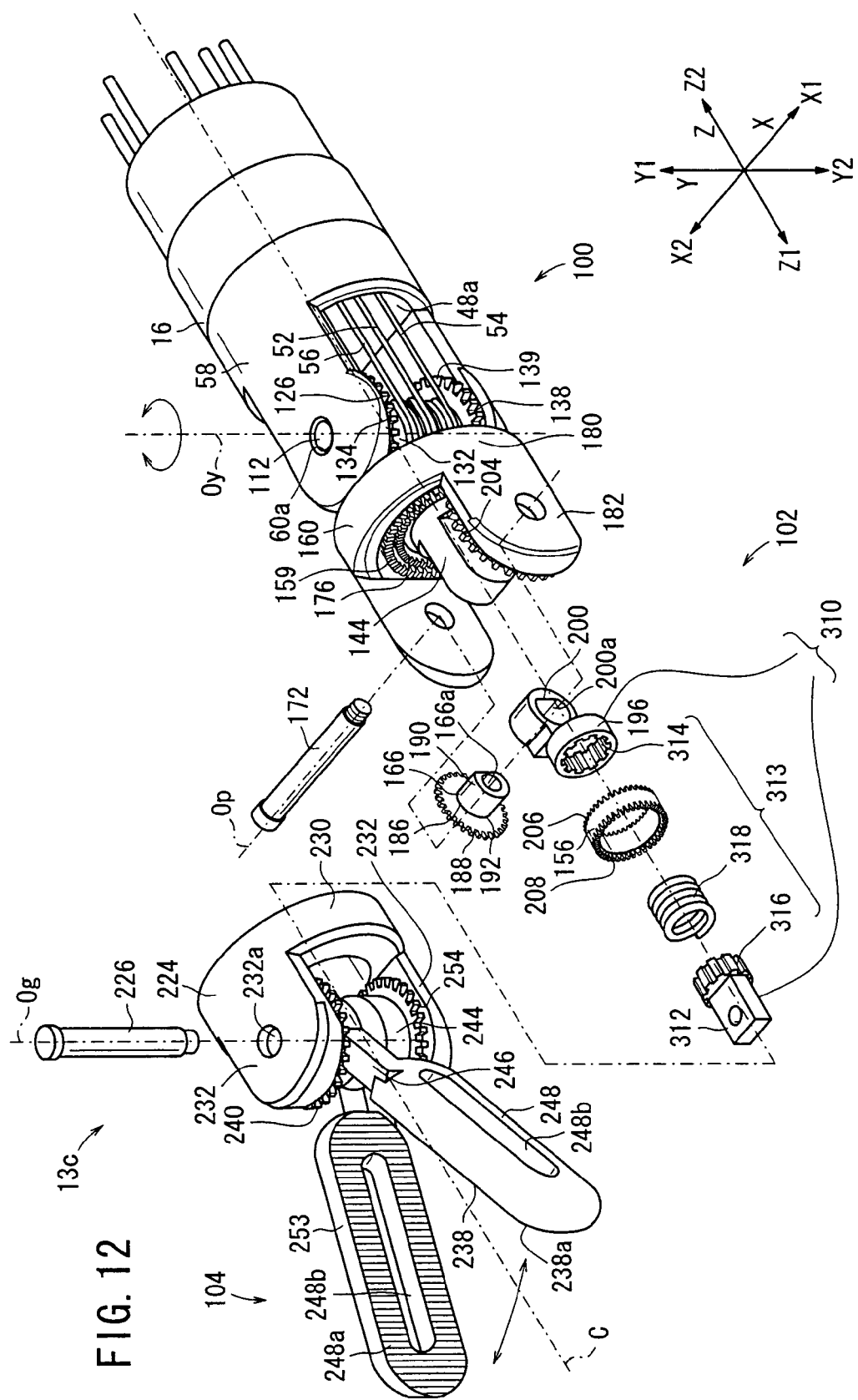
FIG. 12 is an exploded perspective view of a third modification of the working unit according to the first embodiment.

As shown in FIG. 12, a working unit 13c according to a third modification differs from the working unit 12a in that it includes an end effector main shaft 310 in place of the end effector main shaft 170. The end effector main shaft 310 has a gripper base 312 separate from the cylindrical member 196.

The end effector main shaft 310 has an angle adjuster 313 for adjusting the securing pin 226 to any one of a plurality of directions within a plane that lies perpendicularly to the reference axis C. The angle adjuster 313 comprises a splined boss 314 on the inner circumferential surface of the cylindrical member 196, a splined disk 316 mounted on an end face of the gripper base 312 facing the Z2 direction and engaging the splined boss 314, and a helical spring (resilient member) 318 interconnecting the bottom of the splined boss 314 and the end face of the splined disk 316 with connectors, not shown. The splined boss 314 and the splined disk 316 serve as a spline pair and can be angularly adjusted relatively to each other through increments of 45°, for example.

Figure 13:
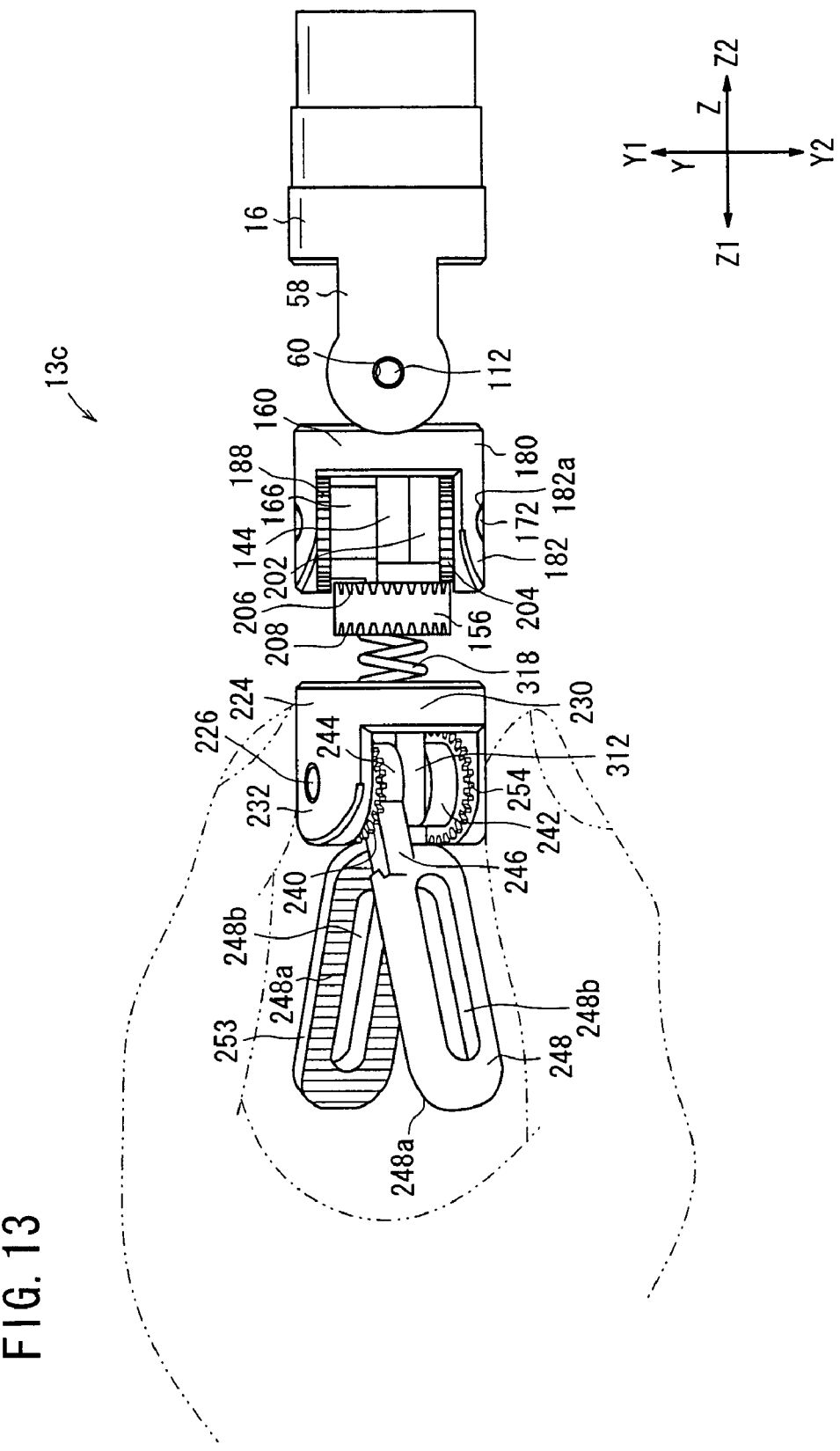
FIG. 13 is a side elevational view of the third modification of the working unit according to the first embodiment, with an end effector being pulled out of a wire-driven mechanism.

The helical spring 318 comprises a tension spring that can be stretched axially. As shown in FIG. 13, when the cover 224 is gripped by fingers and pulled in the Z1 direction, the helical spring 318 is stretched to pull the splined disk 316 out of the splined boss 314. Since the helical spring 318 can elastically be deformed in a torsional direction, too, the drive mechanism 102 and the end effector 104 can be changed in orientation within a plane perpendicular to the reference axis C through increments of 45°, for example, depending on the decision or preference of the surgeon. After the orientation of the drive mechanism 102 and the end effector 104 is changed, the force applied to pull the cover 224 in the Z1 direction is reduced, allowing the drive mechanism 102 and the end effector 104 to be pulled together with the splined disk 316 in the Z2 direction under the resiliency of the helical spring 318. The splined disk 316 is inserted in the selected orientation into the splined boss 314 and engaged thereby.

The working unit 13c is thus capable of adjusting the end effector 104 selectively to a plurality of orientations according to the simple adjusting process which can be performed easily and quickly. The selected orientation of the end effector 104 will not be changed because the splined boss 314 and the splined disk 316 are held in firm engagement with each other against relative angular movement. As the splined disk 316 is attracted in position by the helical spring 318, the splined disk 316 is prevented from being dislodged from the splined boss 314 while the working unit 13c is in use.

Since the helical spring 318 is resilient in torsional directions, if the helical spring 318 has its initial position selected to be a position where the torsional displacement thereof is nil, then the splined disk 316 can easily be returned to the initial position under the torsional resiliency of the helical spring 318.

The helical spring 318 may be made rotatable in torsional directions with respect to at least one of the splined boss 314 and the splined disk 316. If the helical spring 318 is rotatable in torsional directions, then the helical spring 318 will not be twisted on its own, allowing the end effector 104 to be adjusted selectively to a plurality of orientations with lighter forces.

A manipulator 10b according to a second embodiment of the present invention will be described below with reference to FIGS. 14 and 15. The manipulator 10b has an operation command unit 14 and a connector 16 which are identical to the operation command unit 14 and the connector 16 of the manipulator 10a, and includes a working unit 12b instead of the working unit 12a.

Figure 14:
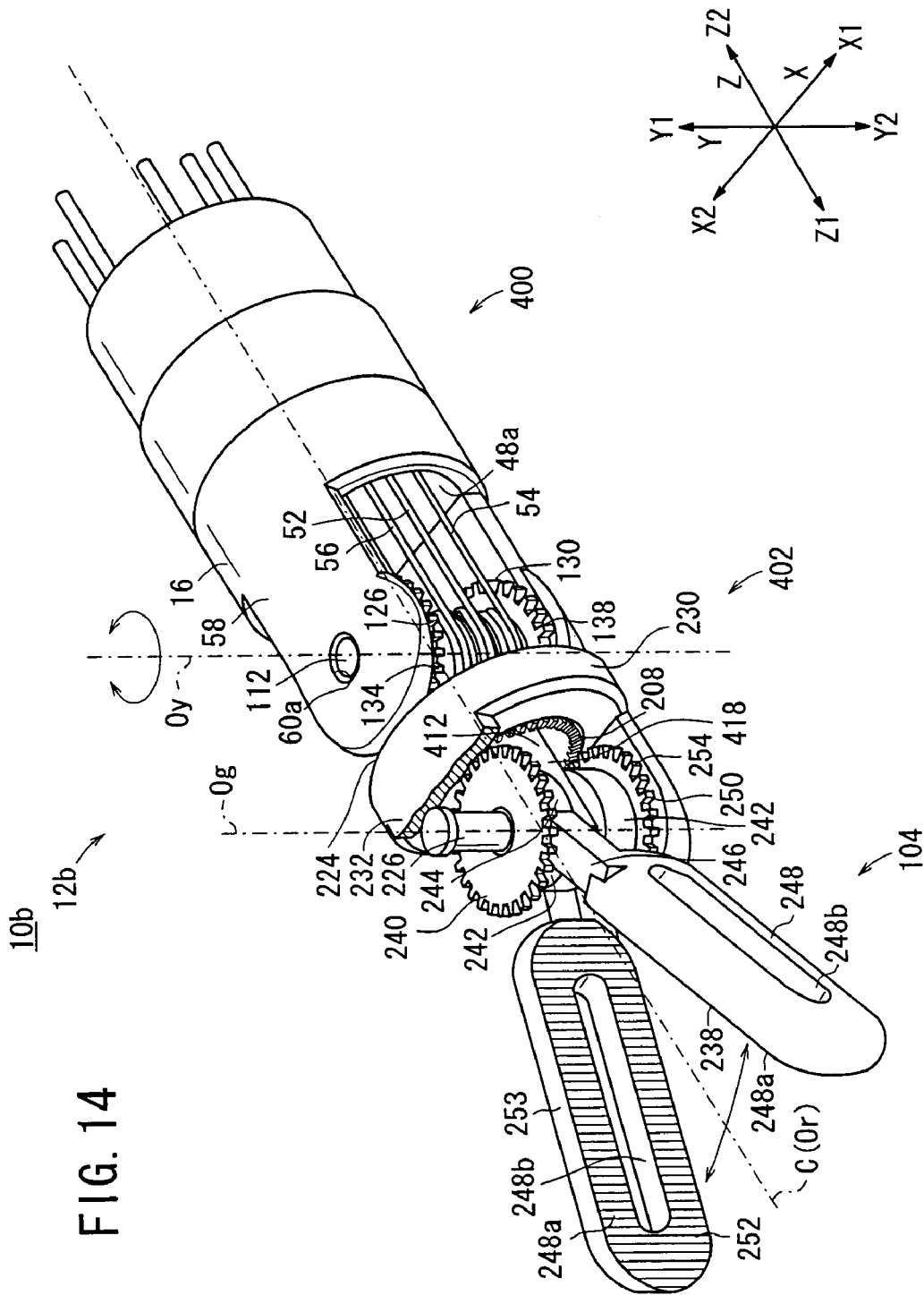
FIG. 14 is a perspective view, partly broken away, of a working unit according to a second embodiment of the present invention.
Figure 15:
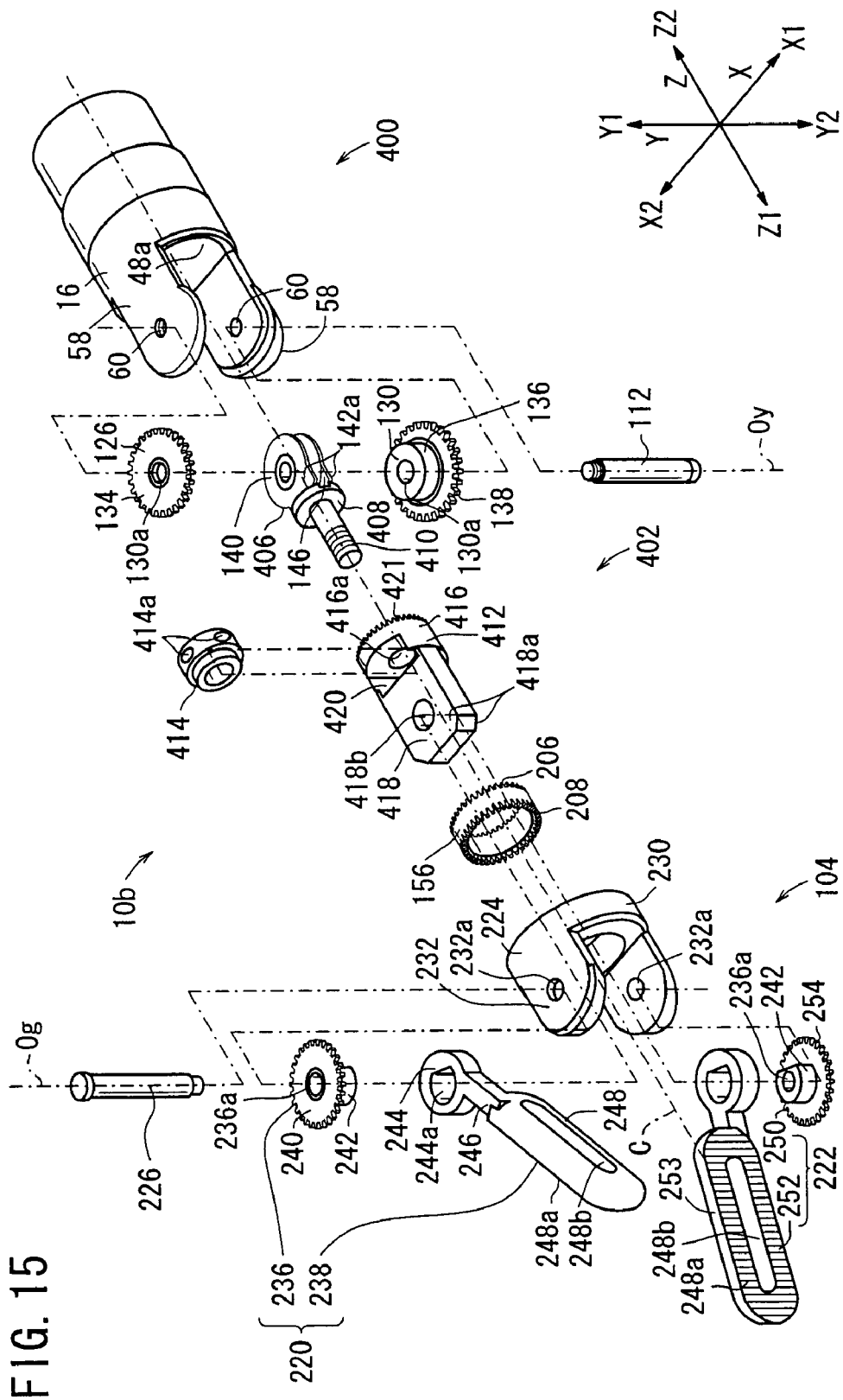
FIG. 15 is an exploded perspective view of the working unit according to the second embodiment.

As shown in FIGS. 14 and 15, the working unit 12b incorporates therein mechanisms of three degrees of freedom. These mechanisms include a mechanism having a first degree of freedom for angularly moving a portion of the working unit 12b that is positioned ahead of a first rotational axis Oy extending along the Y directions, in yawing directions about the first rotational axis Oy, a mechanism having a second degree of freedom for angularly moving the portion of the working unit 12b in rolling directions about a second rotational axis Or extending along the Z directions, and a mechanism having a third degree of freedom for opening and closing an end effector 104 on the distal end of the working unit 12b about a third rotational axis Og symmetrically with respect to a reference axis C. The second rotational axis Or is held in alignment with the reference axis C. The working unit 12b comprises a wire-driven mechanism 400, a drive mechanism 402, and the end effector 104. The end effector 104 is identical in construction to the end effector 104 according to the first embodiment.

The wire-driven mechanism 400 differs from the wire-driven mechanism 100 in that it includes a main shaft 406 in place of the main shaft 128 of the wire-driven mechanism 100. The main shaft 406 has a tubular member 140 through which the shaft 112 extends, an annular seat 408 coupled to the tubular member 140 and facing the Z1 direction, and a support bar 410 extending from the center of the annular seat 408 in the Z1 direction. The support bar 410 is axially aligned with the second rotational axis Or. The support bar 410 has an externally threaded distal end portion.

The drive mechanism 402 comprises a drive base (roll rotor) 412, a fastening nut 414, and a gear ring 156. The fastening nut 414 has a plurality of radial small holes 414a defined therein for inserting a narrow rotary tool.

The drive base 412 includes a tubular member 416 rotatably fitted over a proximal portion of the support bar 410, a gripper base 418 projecting from the tubular member 416 in the Z1 direction, the tubular member 416 and the gripper base 418 defining therebetween a hole 420 extending in the Y directions, and a face gear 421 disposed on an end face of the tubular member 416 which faces the Z2 direction. The face gear 421 is held in mesh with the first gear 134 of the gear body 126.

The tubular member 416 has a hole 416a through which the support bar 410 is inserted. The gear ring 156 is slidably rotatably fitted over the tubular member 416. The support bar 410 has an externally threaded distal end portion inserted through the hole 416a into the hole 420, and the fastening nut 414 is threaded over the externally threaded distal end portion of the support bar 410 in the hole 420. The drive base 412 is thus rotatably supported on the support bar 410 for rotation thereabout.

The gripper base 418, which corresponds to the gripper base 198, includes a pair of vertically spaced parallel slide surfaces 418a for defining opening and closing movement of the gripper and a hole 418b defined in a distal end thereof and extending between the slide surfaces 418a. The hole 418b serves as the center of rotation of the end effector 104. The securing pin 226 is inserted through the hole 418b, and the first end effector body 220 and the second end effector body 222 are pivotally supported on the securing pin 226.

Since the face gear 421 is held in mesh with the first gear 134, when the wire 56 circulatively moves to rotate the gear body 126, the drive base 412 is driven to rotate in rolling directions about the reference axis C. When the drive base 412 rotates in rolling directions, the first end effector body 220 and the second end effector body 222 also rotate in rolling directions.

The working unit 12b allows the end effector 104 to move in yawing and rolling directions independently of the manner in which the end effector 104 operates on its own, i.e., the end effector 104 is opened and closed. As with the working unit 12a, the working unit 12b makes it possible for the end effector 104 to be opened and closed in a wide operating range.

A manipulator 10c according to a third embodiment of the present invention will be described below with reference to FIGS. 16 through 19. The manipulator 10c has an operation command unit 14 and a connector 16 which are identical to the operation command unit 14 and the connector 16 of the manipulator 10a, and includes a working unit 12c instead of the working unit 12a.

Figure 16:
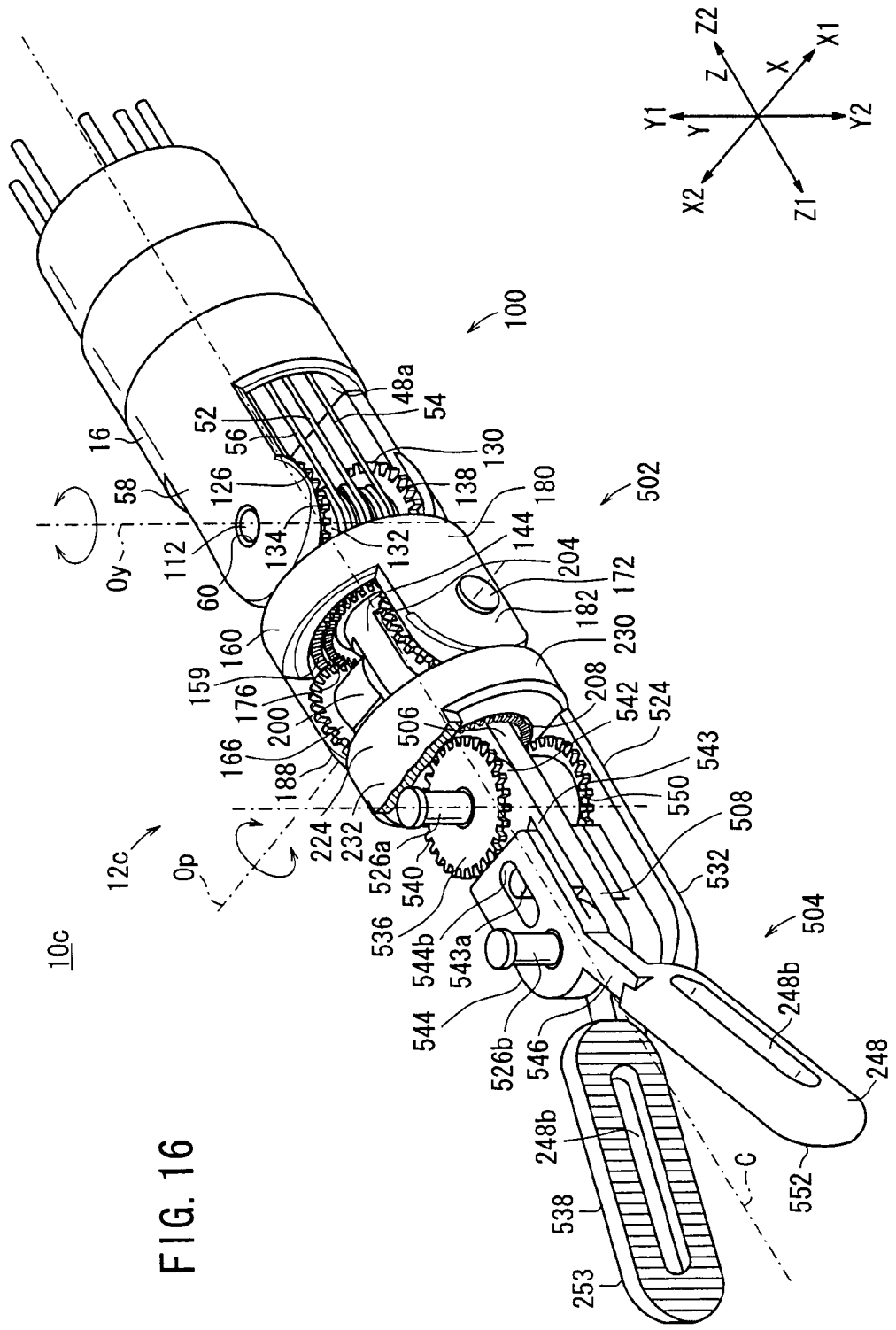
FIG. 16 is a perspective view, partly broken away, of a working unit according to a third embodiment of the present invention.
Figure 17:
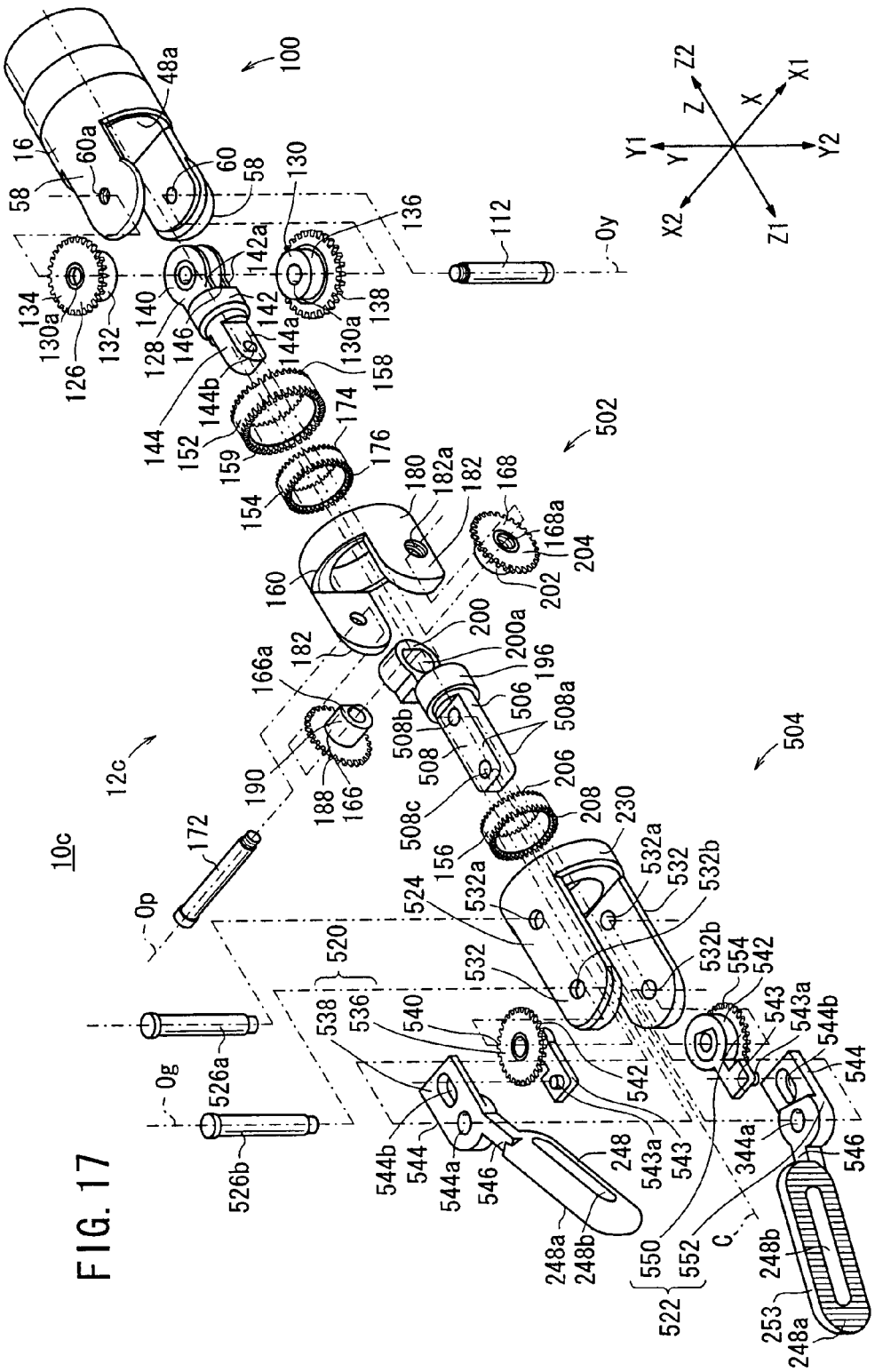
FIG. 17 is an exploded perspective view of the working unit according to the third embodiment.

As shown in FIGS. 16 and 17, like the working unit 12a, the working unit 12c comprises mechanisms of three degrees of freedom for turning an end effector in yawing and pitching directions and opening and closing grippers. The gripper is opened and closed by a link mechanism. The working unit 12c comprises a wire-driven mechanism 100, a drive mechanism 502, and an end effector 504. The wire-driven mechanism 100 is identical to the above wire-driven mechanism 100 according to the first and second embodiments.

The drive mechanism 502 differs from the drive mechanism 102 in that it includes an end effector main shaft 506 in place of the end effector main shaft 170. The end effector main shaft 506 comprises a cylindrical member 196, a gripper base 508 extending in the Z1 direction from the center of the cylindrical member 196, and an engaging member 200.

The gripper base 508 is longer in the Z directions than the gripper base 198. The gripper base 508 has a pair of vertically spaced parallel slide surfaces 508a for defining opening and closing movement of the gripper and a first hole 508b and a second hole 508c defined therein and spaced in the Z directions. The first hole 508b is offset from the second hole 508c in the Z2 direction. The second hole 508c serves as the center of rotation of first and second end effector bodies 520, 522 on the distal end of the gripper base 508.

The end effector 504 comprises a first end effector body 520, a second end effector body 522, a cover 524, a securing pin 526a, and a securing pin (pivot) 526b. The securing pin 526b is aligned with the third rotational axis Og.

The cover 524, which corresponds to the cover 224, includes a short tube 230 and a pair of ears 532 projecting in the Z1 direction from respective opposite upper and lower portions of the short tube 230. The ears 532 are longer than the ears 232 described above. The ears 532 have two pairs of holes 532a, 532b for inserting and securing the securing pins 526a, 526b therein.

The first end effector body 520 comprises a gear body 536 and a working unit (first end effector member) 538. The gear body 536 is positioned in a region between the ears 532 which is displaced in the Y1 direction from the center of the cover 524, and includes a fifth gear 540, a tubular member 542 projecting in the Y2 direction from the center of the fifth gear 540, and a lever arm 543 in the form of a thin plate projecting radially from an end of the tubular member 542 in the Y2 direction. The lever arm 543 of the gear body 536 acts as a first end effector drive member.

A small protrusion 543a having a circular cross section is disposed on the distal end of the surface of the lever arm 543 which faces the Y1 direction. The gear body 536 is oriented such that the fifth gear 540 faces the Y1 direction. The fifth gear 540 is held in mesh with the face gear 208 at its crest in the Y1 direction.

The working unit 538 comprises a link 544 in the form of a thin plate, an arm 546 projecting from the link 544, and a gripper 248 projecting from the arm 546. The gripper 248 (and a gripper 253) is identical in structure to the gripper 248 described above.

The link 544 has a hole 544a for inserting the securing pin 526b therein and an oblong hole 544b for inserting the small protrusion 543a slidably therein, the hole 544a and the oblong hole 544b being juxtaposed in the direction in which the oblong hole 544b extends. The hole 544a is disposed near a region of the link 544 where the link 544 is joined to the arm 546. The oblong hole 544b extends from a position near the hole 544a toward the end of the link 544.

When the securing pin 526b is inserted in the hole 544a, the working unit 538 is swingable about the third rotational axis Og, and the surface of the link 544 which faces the Y2 direction is held against the surface of the lever arm 543 which faces the Y1 direction, with the small protrusion 543a being inserted in the oblong hole 544b. The working unit 538 and the gear body 536 jointly make up a first connector of a link mechanism. The link 544 and the lever arm 543 which are stacked one on the other have a combined thickness that is substantially the same as the thickness of the tubular member 542. The small protrusion 543a has such a height that it does not project from the link 544 or it is lower than the link 544.

The second end effector body 522 comprises a gear body 550 and a working unit (second end effector member) 552. The gear body 550 is positioned in a region between the ears 532 which is displaced in the Y2 direction from the center of the cover 524, and includes a sixth gear 554. The gear body 550 is oriented such that the sixth gear 554 faces the Y2 direction. The sixth gear 554 is held in mesh with the face gear 208 at its crest in the Y2 direction. The gear body 550 is identical in shape to the gear body 536, and the sixth gear 554 corresponds to the fifth gear 540. Other details of the gear body 550 which are identical to those of the gear body 536 are denoted by identical reference characters, and will not be described in detail below. The lever arm 543 of the gear body 550 acts as a second end effector drive member.

The working unit 552 is identical in shape to the working unit 538, and but is in an upside-down orientation with respect to the working unit 538. Details of the working unit 552 which are identical to those of the working unit 538 are denoted by identical reference characters, and will not be described in detail below. The oblong hole 544b and the small protrusion 543a of the second end effector body 522 and the gear body 550 jointly make up a second connector of the link mechanism.

The holes 544a of the working units 538, 552 are aligned with each other as viewed in plan. When the securing pin 526b is inserted in the holes 544a, the working units 538, 552 can be opened and closed symmetrically with respect to the reference axis C.

The gear body 536, the gripper base 508, and the gear body 550 are disposed with substantially no clearances between the ears 532. The securing pin 226b is inserted through the holes 536a, 198c, 536a and supported therein.

Figure 18A:
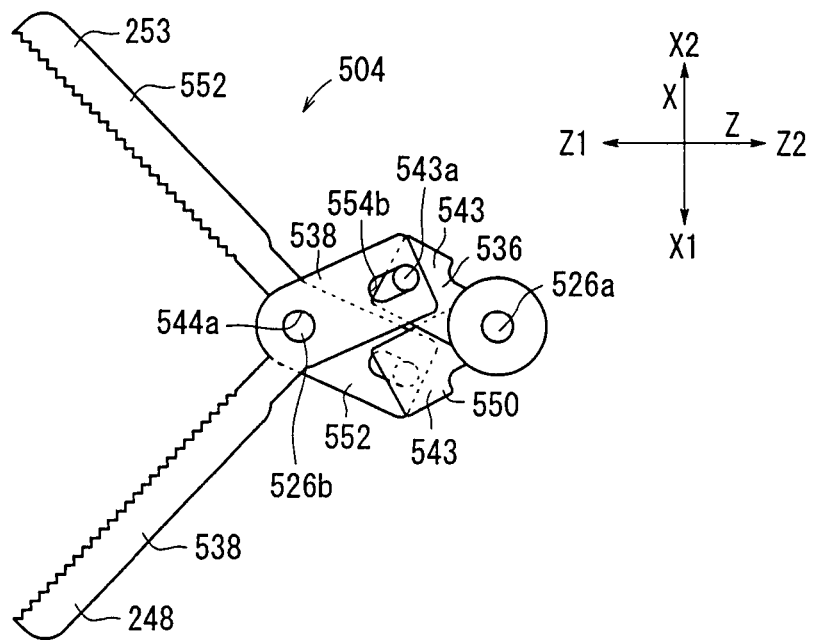
FIG. 18A is a plan view of the working unit according to the third embodiment, with first and second end effector bodies being opened maximally.

As shown in FIG. 18A, when the lever arm 543 of the gear body 536 of the working unit 538 is turned in the X2 direction, the gripper 248 of the working unit 538 is turned in the X1 direction. When the lever arm 543 of the gear body 550 of the working unit 552 is turned in the X1 direction, the gripper 253 of the working unit 552 is turned in the X2 direction. Therefore, the end effector 504 is opened. The end effector 504 is opened maximally when the gear body 536 is rotated clockwise and the gear body 550 is rotated counterclockwise as viewed in plan with the respective small protrusions 534a being held against the ends of the oblong holes 544b in the Z2 direction. As shown in FIG. 18A, when the end effector 504 is opened maximally, it is opened considerably widely. Therefore, the end effector 504 is highly effective in its operation.

Figure 18B:
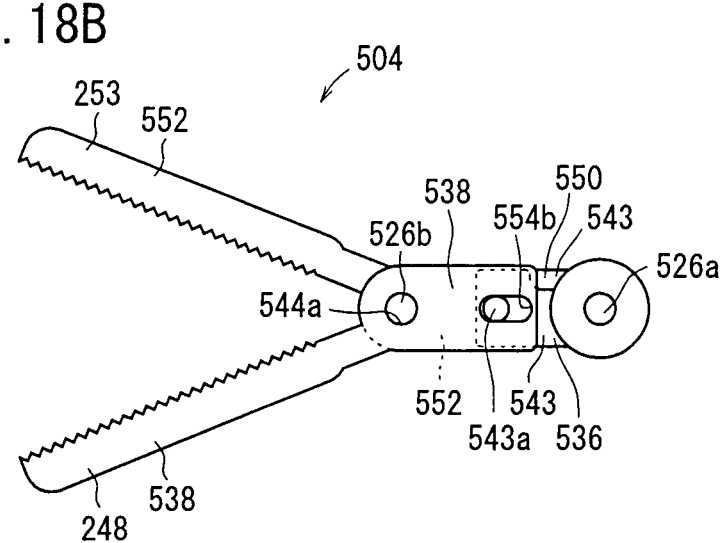
FIG. 18B is a plan view of the working unit according to the third embodiment, with the first and second end effector bodies being in an intermediate position in their opening and closing movement.

As shown in FIG. 18B, when the lever arms 543 of the gear bodies 536, 550 are oriented in substantially the Z1 direction, the grippers 248, 253 are slightly closed. At this time, there are clearances between the small protrusions 534a and the ends of the oblong holes 544b in the Z1 direction.

Figure 18C:
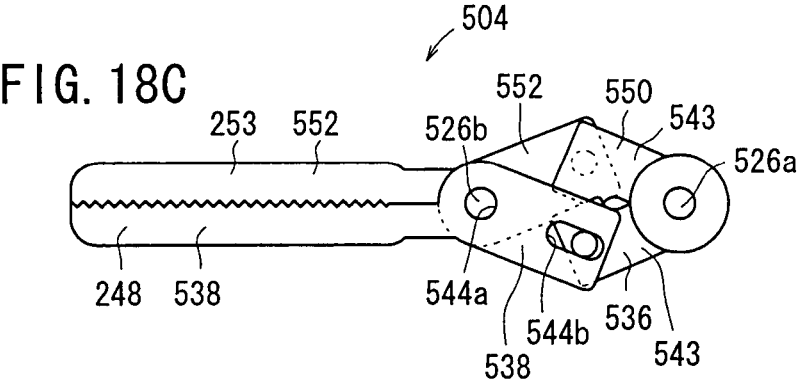
FIG. 18C is a plan view of the working unit according to the third embodiment, with the first and second end effector bodies being closed maximally.

As shown in FIG. 18C, when the lever arm 543 of the gear body 536 of the working unit 538 is turned in the X1 direction, and the lever arm 543 of the gear body 550 of the working unit 552 is turned in the X2 direction, the grippers 248, 253 are oriented in the Z1 direction. Therefore, the end effector 504 is closed. When the inner side surfaces 248a of the grippers 248, 253 are held against each other, there are clearances between the small protrusions 534a and the ends of the oblong holes 544b in the Z2 direction. Consequently, the grippers 248, 253 are reliably closed.

Drive forces applied to open and close the end effector 504 of the working unit 12c will be described below with reference to FIGS. 19A and 19B. It is assumed that the center of the securing pin 526b is represented by O1, the center of the securing pin 526a by O2, the center of the small protrusion 543a by O3, and the distal end of the gripper 248 by O4. Based on these assumptions, some parameters are defined as follows:

$L_A$: the distance from O2 to O3;
$L_B$: the distance from O1 to O3;
$L_C$: the distance from O1 to O4;
$L_D$: the distance from O1 to O2;
$\theta_b$: ∠O1, O2, O3;
$\theta_d$: ∠O1, O3, O2;
$\theta_f$: ∠O2, O1, O3;
$T_A$: the torque applied about O2 to the proximal end of the lever arm 543 (the directions indicated by the arrows in FIGS. 19A and 19B are positive);
$T_B$: the torque applied about O1 to the proximal end of the link 544 (the directions indicated by the arrows in FIGS. 19A and 19B are positive);
$F_A$: the force developed at O2 in a direction perpendicular to the longitudinal direction of the lever arm 543 (the directions indicated by the arrows in FIGS. 19A and 19B are positive);
$F_B$: the force developed at O3 in a direction perpendicular to the longitudinal direction of the link 544 (the directions indicated by the arrows in FIGS. 19A and 19B are positive); and
$F_C$: the force developed at O4 in a direction perpendicular to the longitudinal direction of the gripper 248 (the directions indicated by the arrows in FIGS. 19A and 19B are positive).

The torques and the forces satisfy the following equations (1), (2):

$$T_A = L_A F_A \quad (1)$$

$$T_B = L_B F_B = L_C F_C \quad (2)$$

The following equation (3) is geometrically satisfied:

$$F_A = F_B \sin(\theta_d - \pi/2) \qquad (3)$$

From the equations (1) through (3), the following equations (4), (5) are derived:

$$F_C = F_A(L_B/L_C)(1/\sin(\theta_d - \pi/2)) \qquad (4)$$

$$T_B = T_A(L_B/L_A)(1/\sin(\theta_d - \pi/2)) \qquad (5)$$

The distance $L_B$ and the angle $\theta_d$ are determined from the distance $L_A$, the distance $L_D$, and the angle $\theta_b$ according to the following equations (6), (7):

$$L_B^2 = L_A^2 + L_D^2 - 2L_A L_D \cos\theta_b \qquad (6)$$

$$L_D^2 = L_B^2 + L_A^2 - 2L_A L_B \cos\theta_d \qquad (7)$$

The angle $\theta_f$ is determined according to the equation (8):

$$L_A^2 = L_B^2 + L_D^2 - 2L_B L_D \cos\theta_f \qquad (8)$$

It can be understood from the equation (4) that a power boosting capability is produced if the distance $L_B$ is greater than the distance $L_C$. As indicated by the equation (6), the distance $L_B$ is maximum when the $\theta_b$ is maximum, i.e., when the gripper 248 is closed maximally. Therefore, when the grippers 248, 253 are closed maximally, if the distance $L_B$ is greater than the distance $L_C$, a power boosting capability is produced. Such a relationship is achieved according to the present embodiment.

It can also be understood from the equation (5) that a power boosting capability is produced if the distance $L_B$ is greater than the distance $L_A$. As indicated by the equation (6), since the distance $L_B$ is maximum when the grippers 248, 253 are closed maximally, if the distance $L_B$ is greater than the distance $L_A$ when the grippers 248, 253 are closed maximally, then a power boosting capability is produced. Such a relationship is achieved according to the present embodiment.

It can further be understood from the equations (4), (5) that if the angle $\theta_d$ is not $\pi$, a power boosting capability is produced due to a link angle. Since it is preferable to produce a power boosting capability when the grippers 248, 253 are closed maximally, the angle $\theta_d$ should preferably be not $\pi$ when the grippers 248, 253 are closed maximally. It can be seen that the power boosting capability is very large if the angle $\theta_d$ is close to $\pi/2$. According to the present embodiment, the angle $\theta_d$ should preferably be as close to $\pi/2$ as possible when the grippers 248, 253 are closed maximally.

If the angle $\theta_d$ is not only close to $\pi/2$, but also in the range from $\pi/3(60°)$ to $2\pi/3(120°)$, then the force $F_B$ applied to the distal end of the link 544 is theoretically twice the force $F_A$ generated at the distal end of the lever arm 543. As the power boosting capability (the effect of the toggle mechanism) is produced strongly, the angle $\theta_d$ should be in the range from $\pi/3(60°)$ to $2\pi/3(120°)$ according to the present embodiment.

If the same conditions are satisfied not only when the grippers 248, 253 are closed maximally, but also when the grippers 248, 253 are opened maximally, the same power boosting capability (the effect of the toggle mechanism) is produced. In a surgical process for peeling off a living tissue, for example, the end effector 504 needs to develop a force (referred to as a peeling force) when it is opened maximally. In the state shown in FIG. 19B, the angle $\theta_d$ is in the range from $\pi/3(60°)$ to $2\pi/3(120°)$ when the grippers 248, 253 are opened maximally, thereby developing a large peeling force.

The first end effector body 520 has been described above with reference to FIGS. 19A and 19B. It can easily be understood that the second end effector body 522 is capable of developing the same power boosting capability as the first end effector body 520 and the second end effector body 522 are symmetrical in structure.

A manipulator 10d according to a fourth embodiment of the present invention will be described below with reference to FIG. 20. The manipulator 10d according to the fourth embodiment has an operation command unit 14 and a connector 16 which are identical to the operation command unit 14 and the connector 16 of the manipulator 10a, and includes a working unit 12d instead of the working unit 12a.

Figure 20:
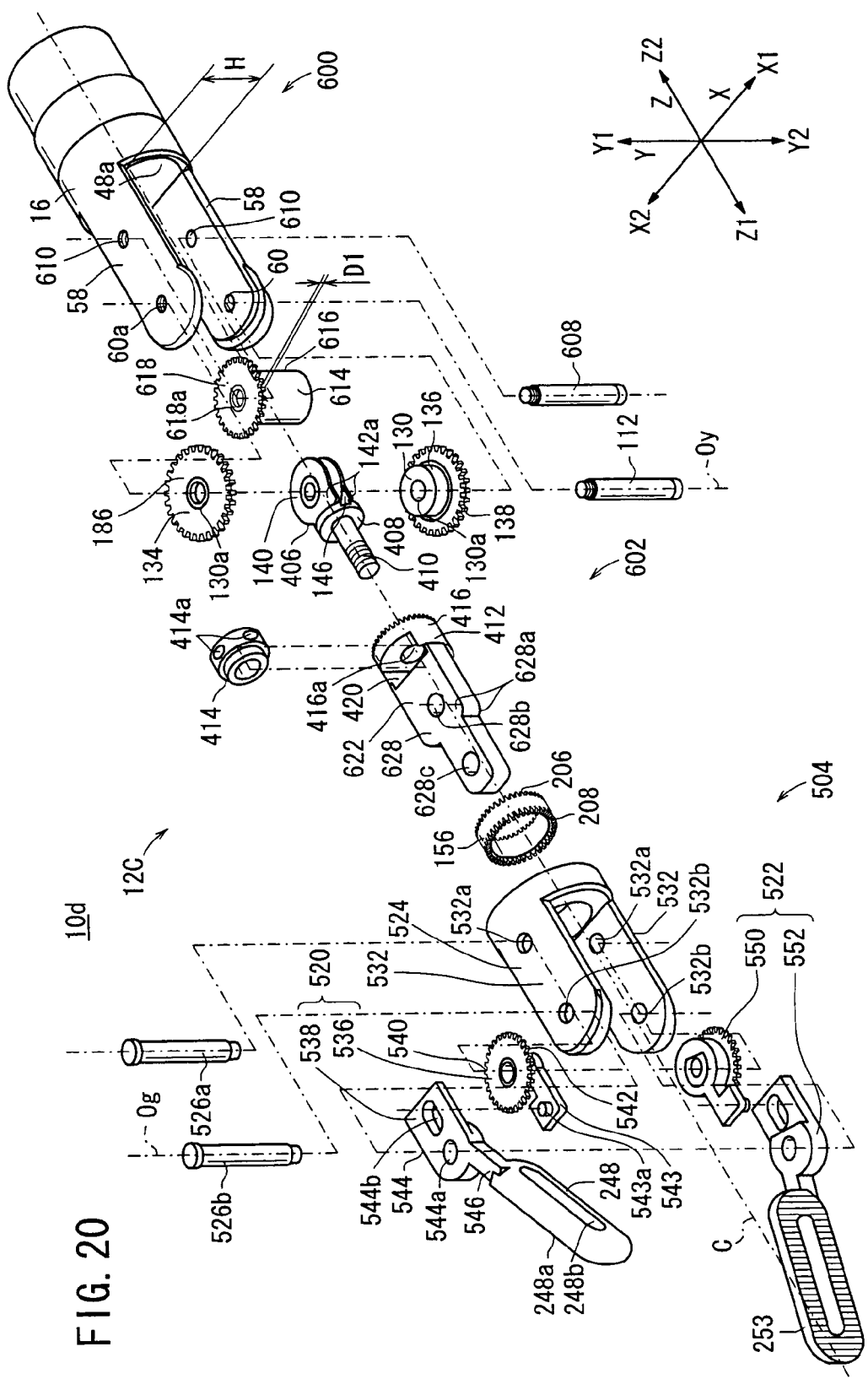
FIG. 20 is an exploded perspective view of a working unit according to a fourth embodiment of the present invention.

As shown in FIG. 20, the working unit 12d incorporates therein mechanisms of three degrees of freedom for turning an end effector in yawing and rolling directions and opening and closing grippers. The working unit 12d includes the mechanism for rotating the end effector in rolling directions in the working unit 12b according to the second embodiment and the toggle mechanism for produce a power boosting capability in the working unit 12c according to the third embodiment. The working unit 12d comprises a wire-driven mechanism 600, a drive mechanism 602, and an end effector 504. The end effector 504 is identical to the end effector 504 described above.

The wire-driven mechanism 600 corresponds to the wire-driven mechanism 400, and additionally includes an auxiliary gear body 614. The auxiliary gear body 614 is disposed in a position offset from the gear body 126, the main shaft 406, and the gear body 130 in the Z2 direction, and lies parallel thereto. The auxiliary gear body 614 is rotatably supported on a shaft 608 which is inserted in holes 610 defined in the respective tongues 58.

The auxiliary gear body 614 comprises a tubular member 616 and an auxiliary gear 618 disposed concentrically on an upper portion of the tubular member 616. The auxiliary gear 618 is larger in diameter than the tubular member 616. The auxiliary gear 618 has a height of about H and is rotatably disposed between the tongues 58. The auxiliary gear 618 has a thickness D1 which is sufficiently smaller than the height H. The height (H-D1) of the tubular member 61 takes up a substantial portion of the height H between the tongues 58. The auxiliary gear 618 has a low annular rib 618a disposed on the upper surface thereof around the hole through which the shaft 608 is inserted. The annular rib 618a prevents the upper surface of the auxiliary gear 618 from contacting the upper tongue 58, thereby reducing the sliding resistance that is imposed on the auxiliary gear 618 by the upper tongue 58.

The auxiliary gear 618 is equal in thickness to the first gear 134 and is held in mesh with the first gear 134. In the wire-driven mechanism 600, the wire 56 is wound around the tubular member 616, and the rotation of the auxiliary gear 618 is transmitted to the gear body 126. The first gear 134 has a greater number of teeth than the auxiliary gear 618, and hence can transmit the rotation of the auxiliary gear 618 at a lower speed (with a higher torque). The rotation of the auxiliary gear 618 may be transmitted at the same speed or a higher speed depending on design conditions.

With the wire-driven mechanism 600, the numbers of turns of the wires 52, 56, the size of the main shaft 406, and the size of the gear body 130, which are positioned forwardly of the tubular member 616, have no adverse effect on the manner in which the wire 56 is wound around the tubular member 616. Accordingly, the wire 56 can wound around the tubular member 616 over a large region thereof. The angular displacement of the auxiliary gear body 614 can thus be increased, allowing the angular displacement and rotational torque of the gear body 126 to be increased. Therefore, the end effector 604 can be angularly moved for a large angular displacement in rolling directions, and can reliably be operated.

The drive mechanism 602 comprises a drive base 622, a fastening nut 414, and a gear ring 156. The drive base 622 comprises a tubular member 416 and a gripper base 628 projecting in the Z1 direction from the tubular member 416, with a hole 420 defined between the tubular member 416 and the gripper base 628 and extending in the Y directions.

The gripper base 628, which corresponds to the gripper base 198, has a pair of upper and lower slide surfaces 628a for defining opening and closing movement of the grippers, and a first hole 628b and a second hole 628c defined therein and juxtaposed in the Z directions. The first hole 628b is offset from the second hole 628c in the Zs direction. The second hole 628c serves as the center of rotation of the first and second end effector bodies 520, 522 on the distal end of the gripper base 628.

The gripper base 628, the first hole 628b, and the second hole 628c correspond respectively to the gripper base 508, the first hole 508b, and the second hole 508c. The distance between the first hole 628b and the second hole 628c is equal to the distance between the first hole 508b and the second hole 508c, i.e., the distance between the securing pin 526a and the securing pin 526b.

Figure 19A:
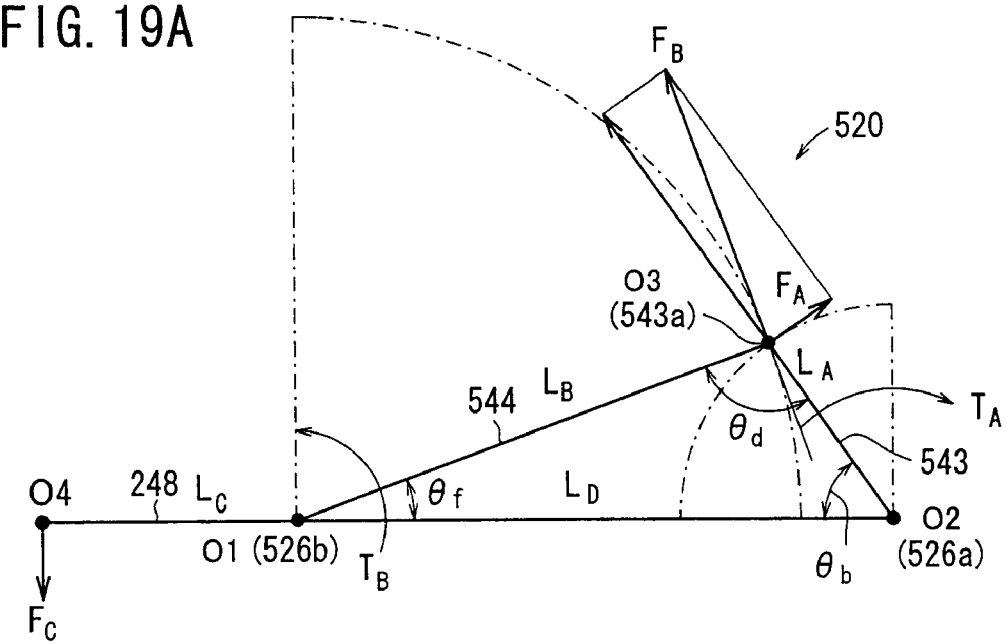
FIG. 19A is a diagram illustrating a power boosting mechanism of the working unit according to the third embodiment, with the first and second end effector bodies being closed maximally.
Figure 19B:
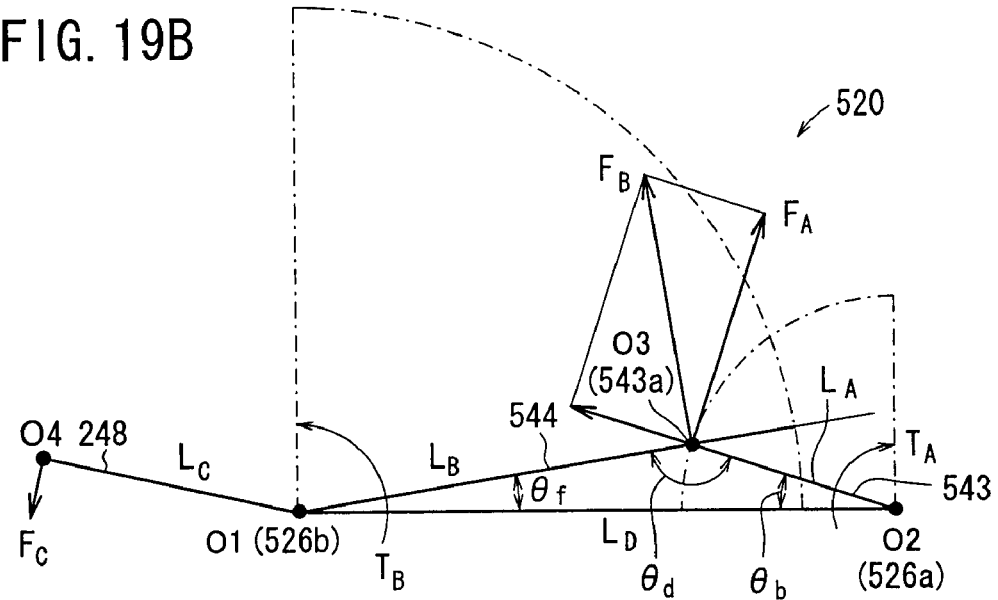
FIG. 19B is a diagram illustrating a power boosting mechanism of the working unit according to the third embodiment, with the first and second end effector bodies being positioned prior to being closed maximally.

The working unit 12d thus constructed is capable of moving the end effector 504 in yawing and rolling directions, and also of providing a power boosting capability for opening and closing the gripper 248 (see FIGS. 19A and 19B).

As described above, the manipulators 10a through 10d and the working units 12a through 12d, 13a through 13c allow the end effector to move in yawing, pitching, or rolling directions independently of the manner in which the end effector operates on its own, i.e., the end effector is opened and closed.

The working units 12a through 12d, 13a through 13c are of a simple structure having three degrees of freedom as with the working unit 900 shown in FIG. 21, but are smaller in size and lightweight than the working unit 900. Therefore, the working units 12a through 12d, 13a through 13c are suitable for use in operations in narrow regions. Since the working units 12a through 12d, 13a through 13c are simple in structure, they are inexpensive to manufacture.

Since the gear ring 156 is of a small-diameter tubular shape, the working units 12a through 12d remain relatively small in diameter. Though the working units 12a through 12d are axially long somewhat because it requires a space for installing the gear ring 156 therein, the axially long working units 12a through 12d do not pose problems as they are a mechanism mounted on the distal end of the elongate connector shaft 48.

The opening and closing movement of the end effector is essentially of a single degree of freedom based on only the motor 42, so that two degrees of freedom based on the other motors 40, 44 can be placed in any desired directions for orienting the end effector in a combination of yawing and pitching (or rolling) directions. In other words, the axes of the working unit can be placed in a pattern suitable for the operation of the manipulator, thereby giving high operability to the manipulator.

Inasmuch as the gear ring 156 is rotatable about the reference axis C and free of obstacles to its rotation, the gear ring 156 is capable of rotating in multiple stages or angles to allow the first end effector drive member and the second end effector drive member to move in a wide operating range.

The manipulators 10a through 10d and the working units 12a through 12d have been illustrated as being used in the medical application. However, they can also be used in applications to repair narrow regions of energy-related devices and apparatus, and are also applicable to remote control mechanisms for performing techniques on the patient from locations spaced from the patient through electric communication means or the like. It can easily be understood that the grippers 248, 253 of the working units 12a through 12d may be changed in shape and structure into any of various tools including a pliers, a nipper, an end nipper, etc. In each of the embodiments, the combinations of spur gears and face gears may be replaced with combinations of other elements, e.g., bevel gears, insofar as they can transmit the rotational power through their mutual contact while changing the rotational direction.

In anticipation of the embodiments described above, the applicant had developed a working unit 900 shown in FIG. 21.

As shown in FIG. 21, the working unit 900 is actuated by a wire 902, a wire 903, and a wire 904 and has three degrees of freedom. The wires 902, 903, 904 are wound around respective tubular bodies 940c, 940b, 940a.

In the working unit 900, the wires 902, 904 are operated to rotate a bear 905, which rotates a face gear, not shown, to rotate the distal end of the working unit 900 in a rolling direction. The wire 904 is operated to rotate a second gear 906, which causes a gear ring 907 and a gear 908 to open and close a gripper 909. The wires 902, 903, 904 are operated to cause a main shaft 910 to rotate the distal end in a yawing direction.

Although certain preferred embodiments of the present invention have been shown and described in detail, it should be understood that various changes and modifications may be made therein without departing from the scope of the appended claims.

What is claimed is:

1. A working mechanical device comprising:
a first drive rotor rotatable about a pivot axis extending in a direction perpendicular to a reference axis;
a first intermediary rotor including an axial proximal end surface held in contact with said first drive rotor, and rotatable about said reference axis to change the direction of rotation of said first drive rotor;
a first gear held in contact with an axially distal end surface of said first intermediary rotor at one side of the center thereof, and rotatable about an opening and closing axis perpendicular to said reference axis by rotation of the first intermediary rotor to change the direction of rotation of said first intermediary rotor;
a first working unit connected to the first gear and rotatable about the opening and closing axis integrally with the first gear;
a second gear held in contact with an axially distal end surface of said first intermediary rotor at an opposite side of the center thereof, and rotatable in a direction opposite to the direction in which said first gear rotates, about the opening and closing axis perpendicular to said reference axis by rotation of the first intermediary rotor to change the direction of rotation of said first intermediary rotor;
a second working unit connected to the second gear and rotatable about the opening and closing axis integrally with the second gear;
an end effector rotor rotatable about the pivot axis; and
an end effector main shaft connected to the end effector rotor and rotatable about the pivot axis integrally with the end effector rotor;
wherein, of the first drive rotor and the end effector rotor, only the first intermediate rotor is held in engagement with the first drive rotor, and
wherein in accordance with the end effector rotor and the end effector main shaft rotating about the pivot axis, an end effector including the first working unit and the second working unit moves about the pivot axis.

2. A working mechanical device according to claim 1, further comprising:
at least one rotational unit disposed on a proximal end side including the position of said first drive rotor, and disposed in either an orientation parallel to said opening and closing axis or an orientation perpendicular to said opening and closing axis and said reference axis.

3. A working mechanical device according to claim 1, further comprising:
a second drive rotor rotatable in a direction perpendicular to said reference axis; and
a roll rotor including an axial proximal end surface held in contact with said second drive rotor, and rotatable about said reference axis to change the direction of rotation of said second drive rotor;
wherein said first gear and said second gear are mounted on said roll rotor for angular movement about said reference axis in response to rotation of said second drive rotor.

4. A working mechanical device according to claim 1, wherein the rotational axis of said first drive rotor and said opening and closing axis extend obliquely to each other rather than extending in parallel or perpendicular directions.

5. A working mechanical device according to claim 1, further comprising
an angle adjuster for adjusting said opening and closing axis to any one of a plurality of directions within a plane lying perpendicularly to said reference axis.

6. A working mechanical device according to claim 5, wherein said angle adjuster comprises:
a spline pair; and
a resilient member for attracting said spline pair to insert a shaft thereof into a boss;
wherein said resilient member is axially stretchable and elastically deformable or rotatable in a torsional direction.

7. A working mechanical device according to claim 1, further comprising:
a first end effector member and a second end effector member which are actuatable respectively by said first gear and said second gear; and
a pivot by which said first end effector member and said second end effector member are angularly movably supported;
wherein said first gear and said second gear rotate in opposite directions around said pivot; and
said first gear and said first end effector member are connected to each other by a first connector and said second gear and said second end effector member are connected to each other by a second connector, each of said first connector and said second connector comprising a pin and an oblong hole, said pin being slidably guided in said oblong hole.

8. A working mechanical device according to claim 1, further comprising:
a driven tubular member rotatable about its own axis by a flexible power transmitting member wound therearound; and
a second intermediary rotor including an axial proximal end surface held in contact with said driven tubular member, and rotatable about said reference axis to change the direction of rotation of said driven tubular member;
wherein said first drive rotor is rotatable in contact with an axial distal end surface of said second intermediary rotor.

* * * * *